(12) United States Patent
Pastron

(10) Patent No.: US 8,715,171 B2
(45) Date of Patent: May 6, 2014

(54) INSERTION AID DEVICE

(75) Inventor: Nicholas J. Pastron, Long Island City, NY (US)

(73) Assignee: NJR Medical, Inc., Long Island City, NY (US)

( * ) Notice: Subject to any disclaimer, the term of this patent is extended or adjusted under 35 U.S.C. 154(b) by 210 days.

(21) Appl. No.: 13/171,151

(22) Filed: Jun. 28, 2011

(65) Prior Publication Data

US 2013/0006057 A1  Jan. 3, 2013

(51) Int. Cl.
*A61B 1/267* (2006.01)

(52) U.S. Cl.
USPC ........................................................ 600/187

(58) Field of Classification Search
USPC .......... 600/185, 187, 188, 190, 193, 194, 199
See application file for complete search history.

(56) References Cited

U.S. PATENT DOCUMENTS

| | | | |
|---|---|---|---|
| 1,613,373 A | 1/1927 | Beck | |
| 2,127,215 A | 8/1938 | Gwathmey | |
| 2,756,742 A | 7/1956 | Barton | |
| 3,926,196 A | 12/1975 | Bornhorst et al. | |
| 4,041,937 A | 8/1977 | Diaz | |
| 4,148,308 A | 4/1979 | Sayer | |
| 4,213,451 A | 7/1980 | Swenson | |
| 4,306,547 A | 12/1981 | Lowell | |
| 4,802,851 A | 2/1989 | Rhoades | |
| 4,883,426 A | 11/1989 | Ferrer | |
| 4,982,729 A | 1/1991 | Wu | |
| 5,025,806 A | 6/1991 | Palmer et al. | |
| 5,060,646 A | 10/1991 | Page | |
| 5,085,633 A | 2/1992 | Hanifi et al. | |
| 5,151,094 A | 9/1992 | Hanifi | |
| 5,215,522 A | 6/1993 | Page et al. | |
| 5,220,916 A | 6/1993 | Russo | |
| 5,378,226 A | 1/1995 | Hanifi et al. | |
| 5,394,865 A | 3/1995 | Salerno | |
| 5,694,922 A | 12/1997 | Palmer | |
| 5,845,634 A | 12/1998 | Parker | |
| 6,012,451 A | 1/2000 | Palmer | |
| 6,162,170 A | 12/2000 | Foley et al. | |
| 6,176,823 B1 * | 1/2001 | Foley et al. | 600/114 |
| 6,176,824 B1 | 1/2001 | Davis | |

(Continued)

FOREIGN PATENT DOCUMENTS

WO   WO 2013002832   1/2013

OTHER PUBLICATIONS

Non Final Office Action in Related U.S. Appl. No. 12/886,971 dated Mar. 13, 2013, 11 pages.

(Continued)

*Primary Examiner* — Pedro Philogene
*Assistant Examiner* — David Comstock
(74) *Attorney, Agent, or Firm* — Kilpatrick Townsend & Stockton LLP

(57) ABSTRACT

Described are insertion aid devices including a handle, a tongue depressor, a first passageway, and a guide with a recess formed by a pair of prongs. The first passageway includes an entry portal and an exit portal, and may also include an alternative entry portal. The insertion aid devices may also include one or more additional passageways, each with an entry portal and an exit portal. The additional passageway may be formed by a plurality of C-clips or a shelf. The tongue depressor may be pivotally coupled to the handle.

20 Claims, 19 Drawing Sheets

(56) References Cited

U.S. PATENT DOCUMENTS

| | | |
|---|---|---|
| 6,238,213 B1 | 5/2001 | Young et al. |
| 6,277,200 B2 | 8/2001 | Xia et al. |
| 6,500,142 B1 | 12/2002 | Harreld et al. |
| 7,827,985 B2 | 11/2010 | Pastron |
| 2004/0019256 A1 | 1/2004 | Cubb et al. |
| 2005/0065411 A1 | 3/2005 | Baldwin et al. |
| 2005/0090712 A1 | 4/2005 | Cubb |
| 2005/0240081 A1 | 10/2005 | Eliachar |
| 2006/0036133 A1 | 2/2006 | Demsky |
| 2006/0065268 A1 | 3/2006 | Koyama et al. |
| 2007/0093693 A1* | 4/2007 | Geist et al. .................... 600/199 |
| 2007/0106122 A1 | 5/2007 | Yokota et al. |
| 2007/0272258 A1* | 11/2007 | Pastron ........................ 128/860 |
| 2011/0060192 A1 | 3/2011 | Pastron |

OTHER PUBLICATIONS

International Search Report and Written Opinion in Related PCT Application No. PCT/US2011/067741, dated Oct. 22, 2012, 26 pages.

Final Office Action in related U.S. Appl. No. 12/886,971 dated Aug. 29, 2013, 10 pages.

International Preliminary Report on Patentability in Related Application PCT/US2011/067741, dated Jan. 16, 2014, 12 pages.

Response to Final Office Action in Related U.S. Appl. No. 12/886,971, dated Dec. 30, 2013, 12 pages.

\* cited by examiner

INSERTION AID DEVICE

FIELD OF THE INVENTION

The invention relates to a method and apparatus for maintaining the patient's mouth in an open position for oral cleaning and suctioning, orotracheal suctioning, and orogastric tube insertion, for uncoiling nasotracheal suctioning catheters and nasogastric tubes within the mouth during insertion, and for inserting orotracheal suctioning catheters.

BACKGROUND OF THE INVENTION

Oral cleaning instruments, oral suctioning instruments, and tracheal suctioning catheters are commonly used in health care patients with respiratory distress, critical illness, chronic illness, terminal illness, weakness, paralysis, or any patient requiring breathing support from a ventilator.

To perform oral cleaning, most caregivers use foam swabs with various antiseptic solutions to clean and moisten a patient's mouth. Oral suctioning is commonly performed by inserting a rigid plastic tube, often called a Yankauer suction, into a patient's mouth and throat to suction out saliva and mucus. The purpose of oral cleaning and oral suctioning is to remove bacteria that builds up in the mouth of patients who are unable to perform oral care, such as brushing their teeth. Various studies have shown that the buildup of bacteria in patients who are unable to perform oral care increases their risk of the nosocomial pneumonias, hospital acquired pneumonia ("HAP") and ventilator associated pneumonia ("VAP"), due to the aspiration of saliva and secretions with high levels of bacteria.

Tracheal suctioning is commonly performed to suction out secretions when a patient is too weak to cough up secretions on their own. Tracheal suctioning may be performed via either nasotracheal suctioning or orotracheal suctioning. In either case, a tracheal suction catheter is used, which typically is a soft, pliable plastic or rubber tube. In the case of nasotracheal suctioning, the tracheal suction catheter is inserted into the naris and continues down the trachea. Once the tracheal suction catheter reaches the trachea, the unwanted secretions are suctioned out. The nasotracheal suctioning method can cause trauma and bleeding to the nasal area. In addition, the suction catheter also has a tendency to coil in the back of the throat and may trigger the patient's gag reflex.

Typically, orotracheal suctioning is attempted in patients with increased coagulation times, nasal fractures, or deviated septums, or if coiling continues to occur in the nasotracheal approach. To perform orotracheal suctioning, the tracheal suction catheter is inserted into the mouth and continues down the trachea. Once the tracheal suction catheter reaches the trachea, the unwanted secretions are suctioned out. Similar to the nasotracheal suctioning method, the suction catheter has a tendency to coil in the back of the throat and may trigger the patient's gag reflex.

Patients are usually in an altered mental state from sedation, confusion, or being frightened and sometimes do not cooperate for oral cleaning, oral suctioning, and tracheal suctioning. Patients sometimes bite down on the cleaning and suctioning instruments, which can stop the oral cleaning, oral suctioning, and tracheal suctioning processes, and sometimes break a piece of the instrument off in the patient's mouth or even bite caregivers' fingers. Other problems that exist include instrument insertion trauma to the nose or mouth and the spread of bacteria from the mouth to the lungs during tracheal suctioning.

Additionally, at times, it may be beneficial to employ more than one catheter or similar device when assisting a patient. Such situations may arise by intent by the medical personnel or by necessity given a problem with the first catheter. For example, a medical professional may desire to insert a sinus scope, biopsy tool, a fiberoptic scope, camera, saline flush or lavage, various medications, or cauterizing tool, in addition to the first catheter. Alternatively, the first catheter may become clogged or otherwise malfunction, in which it may be advantageous to be readily able to insert a second catheter.

Nasogastric tubes and orogastric tubes are commonly used in the course of health-care, most frequently in the preparation before, during, and after surgery, for tube feedings, and in healthcare patients with stomach decompression or other stomach and bowel issues. Typically, these nasogastric/orogastric tubes are formed from resilient plastic material such as polyurethane, polyethylene, or silicone polymer. In addition, these tubes may be manufactured from surgical steel. The nasogastric and orogastric tubes typically have a proximal end, a distal end, and a central lumen or passageway. Further details about such tubes can be found in U.S. Pat. Nos. 4,778,448 and 4,634,425, the disclosures of which are incorporated herein by reference.

Nasogastric tubes and orogastric tubes are either inserted in the mouth or nose, down the throat, and into the stomach. The nasogastric and orogastric tubes have been a problem for patients and clinicians for some time. When a nasogastric tube is inserted into the patient's nose, sometimes the tube coils in the back of the throat and may trigger the patient's gag reflex. Similar to the problems experienced with the oral cleaning, oral suctioning, and tracheal suctioning, patients sometimes bite down on the orogastric tubes, which can stop the process, and sometimes break a piece of the tube off in the patient's mouth or even bite caregivers' fingers.

In addition to the types of suctioning described above, patients requiring such suctioning may also be faced with additional medical crises in which the patient requires intubation. In those unfortunate situations, the caregiver has typically been forced to use to different devices to perform the suctioning and then the intubating, which delays the overall completion of the procedures at a time when every second counts.

SUMMARY

Embodiments of the present invention include an insertion aid device with a handle comprising a distal end, a tongue depressor, a first passageway, and a guide with a recess formed by a pair of prongs that extend from the distal end of the tongue depressor. Alternative embodiments may further comprise at least one additional passageway.

The tongue depressor includes a proximal end coupled to the distal end of the handle and a distal end, wherein the tongue depressor has a progressively smaller cross-sectional shape from the proximal end to the distal end. In some embodiments, the tongue depressor may be pivotally coupled to the handle.

The first passageway includes an entry portal and an exit portal. In some embodiments, the entry portal may be positioned adjacent the proximal end of the tongue depressor, while in other embodiments the entry portal may be positioned adjacent the handle. The exit portal may be positioned adjacent the distal end of the tongue depressor. In some embodiments, the first passageway may also include at least one alternative entry portal.

The additional passageway includes an entry portal and an exit portal. In some embodiments, the entry portal may be positioned adjacent the proximal end of the tongue depressor, while in other embodiments the entry portal may be positioned adjacent the handle. The exit portal may be positioned adjacent the distal end of the tongue depressor. In some embodiments, the additional passageway may be formed by a plurality of C-clips or a shelf.

BRIEF DESCRIPTION OF THE DRAWINGS

The invention may be understood by reference to the following description taken in conjunction with the accompanying drawings, in which, like reference numerals identify like elements, and in which.

DETAILED DESCRIPTION

Figure 1:
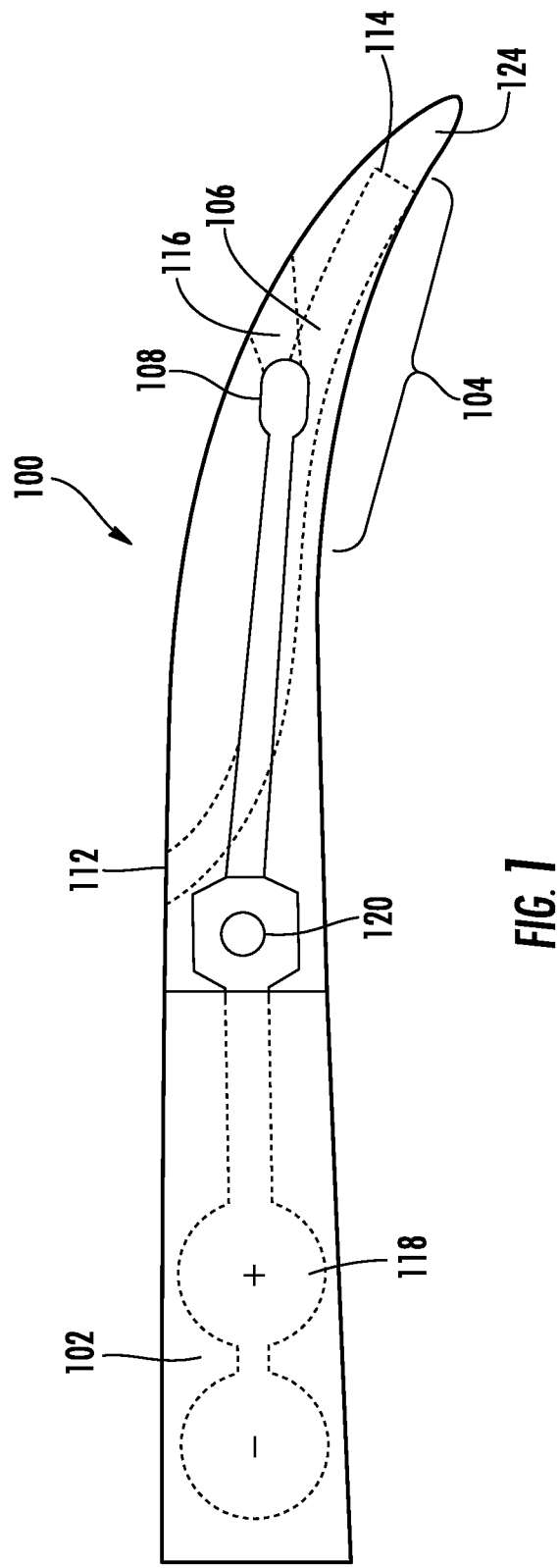
FIG. 1 is a side view of an insertion aid device according to one embodiment of the present invention.

FIGS. 1-6 illustrate one embodiment of an insertion aid device 100. Alternative embodiments of the insertion aid device 100 are shown in FIGS. 7-19. The insertion aid device 100 comprises a handle 102, a tongue depressor 104, a first passageway 106, a light source 108, and a guide 110.

In the embodiments illustrated in FIGS. 1-19, the handle 102 may be constructed of a rigid material, such as plastic, steel, or any other suitable material. The handle 102 may have a circular cross-section or other suitable cross-sectional shape including but not limited to rectilinear, oval, crescent, triangular, pentagonal, hexagonal, octagonal, D-shaped, and I-shaped. However, one of skill in the relevant art will understand that the handle 102 may have any appropriate shape that allows a caregiver to use the insertion aid device 100 to accomplish the desired task without risk of injury to the patient or the caregiver. In some embodiments, the handle 102 may include a textured surface to prevent the insertion aid device 100 from slipping during use. In other embodiments, the handle 102 may include indentations for the caregiver's fingers when the handle 102 is grasped.

The tongue depressor 104 is adjacent the handle 102, as illustrated in FIGS. 1-19. In some embodiments, the tongue depressor 104 is integrally formed with the handle 102. In other embodiments, such as the embodiment illustrated in FIGS. 15 and 16, the tongue depressor 104 is coupled to the handle 102 and may be formed of the same or different materials than the handle 102. For example, in some embodiments, the tongue depressor 104 may be constructed from rigid material such as plastic, steel, or any other suitable material, while the handle 102 is formed of similar or other materials. In other embodiments, the tongue depressor 104 is constructed of a flexible material such as rubber or soft plastic, or a moldable material, molded with the use of the material itself, or molded with the use of a stylette, while the handle 102 is formed of similar or other materials. In the embodiments shown in FIGS. 1-19, the tongue depressor 104 has a curved shape that approximately corresponds to the shape of the lower surface of a patient's mouth and tongue. In some embodiments, such as the embodiments illustrated in FIGS. 1-14 and 17-19, the tongue depressor 104 is configured to contact a patient's mouth cavity without entering the patient's throat. In these embodiments, the tongue depressor 104 includes a declining surface along its length to aid in the depression of the tongue and to aid in the insertion of the insertion aid device 100. The tongue depressor 104 also has a progressively reducing cross-sectional shape, which becomes increasingly smaller in the direction of the distal end. However, one of skill in the relevant art will understand that the tongue depressor 104 may have any appropriate shape that allows a caregiver to use the insertion aid device 100 to accomplish the desired task without risk of injury to the patient or the caregiver.

As shown in FIGS. 1-2, 4, 7-14 and 17-19, the first passageway 106 is coupled to the tongue depressor 104 and positioned proximate at least a portion of the longitudinal axis of the insertion aid device 100. However, one of skill in the art will understand that any appropriate orientation of the first passageway 106 may be used with the insertion aid device 100. For example, in some embodiments, the first passageway 106 may be positioned along an external surface of the tongue depressor 104. In other embodiments, such as the embodiments illustrated in FIGS. 1-2, 4, 7-14, and 17-19, the first passageway 106 is contained within the insertion aid device 100. In some embodiments, such as the embodiments illustrated in FIGS. 1-2, 4, 7-8, 10-14, and 18-19, the first passageway 106 includes an entry portal 112, which is located adjacent the proximal end of the tongue depressor 104. In other embodiments, such as the embodiment illustrated in FIGS. 9 and 17, the entry portal 112 is located adjacent the handle 102 to allow for better access to the entry portal 112. The first passageway 106 may also include an exit portal 114 adjacent the distal end of the tongue depressor 104. In some embodiments, such as the embodiment illustrated in FIG. 17, the first passageway 106 further includes at least one alternative entry portal 156, in addition to the entry portal 112. The alternative entry portal 156 allows the caregiver to access the first passageway 106 from a location other than the entry portal 112. This additional access point may expedite the medical procedures performed by the caregiver and may be useful in instances in which a problem occurs with the entry portal 112, such as clogging, in which a saline flush or medication lavage can be used to flush out the clog. In some embodiments, the alternative entry portal 156 may be adjacent the handle 102. In other embodiments, such as the embodiment illustrated in FIG. 17, the alternative entry portal 156 may be adjacent the proximal end of the tongue depressor 104.

In alternative embodiments, such as the embodiments illustrated in FIGS. 7, 10, 12-14, and 18-19, the entry portal 112 includes an angled projection 131 to facilitate insertion of the tracheal suction catheter 126, or other similar device, by allowing the caregiver to insert the tracheal suction catheter 126, or other similar device, at an angle that is less than 90 degrees from the central axis of the handle 102. In some embodiments comprising the alternative entry portal 156, such as the embodiment illustrated in FIG. 17, the alternative entry portal 156 may also include an angled projection 157 to facilitate insertion of the tracheal suction catheter 126, or other similar device, by allowing the caregiver to insert the tracheal suction catheter 126, or other similar device, at an angle that is less than 90 degrees from the central axis of the handle 102.

Figure 8:
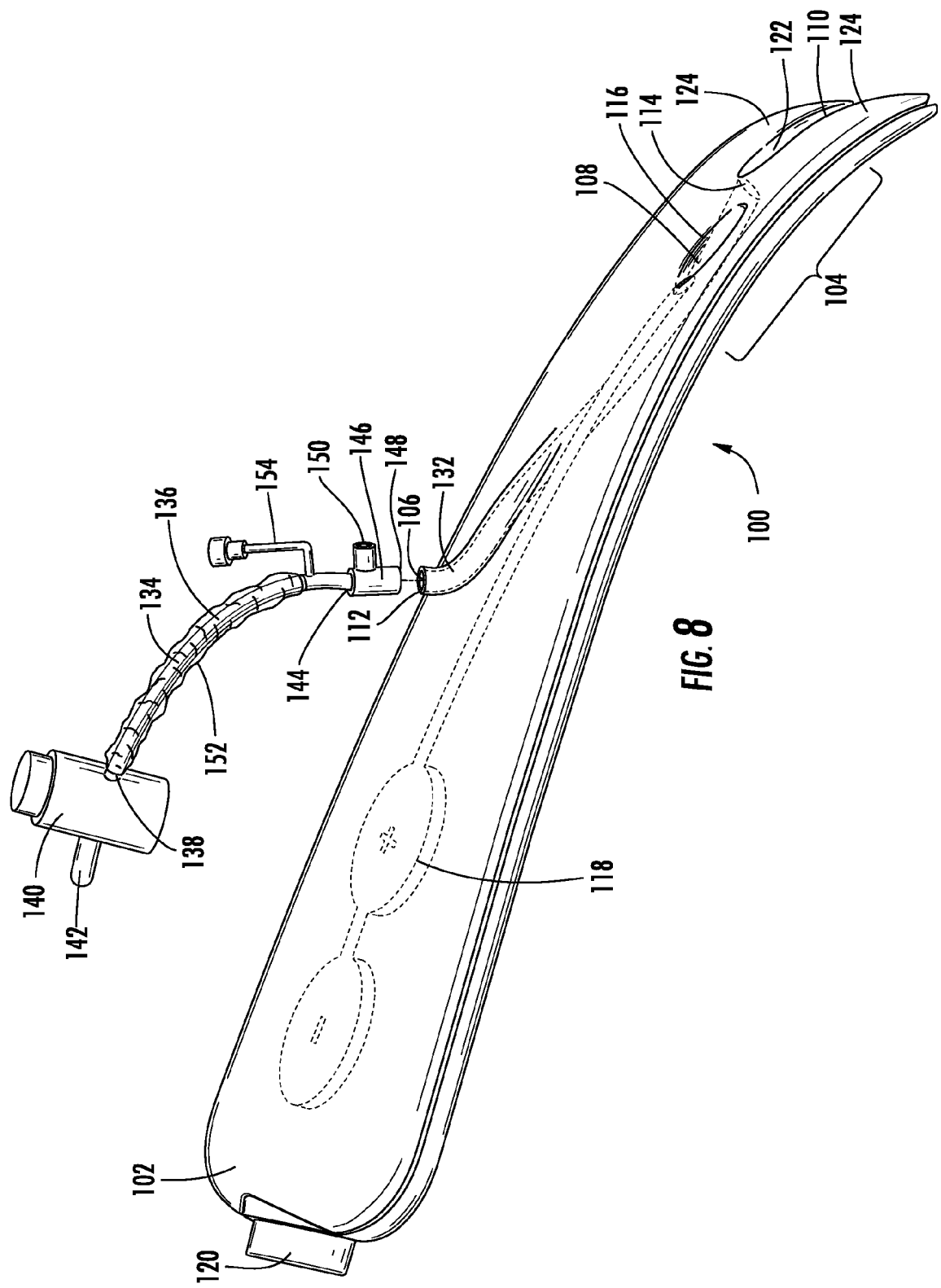
FIG. 8 is a perspective view of an insertion aid device according to another alternative embodiment of the present invention with an in-line suction catheter.

In another alternative embodiment shown in FIG. 8, the first passageway 106 includes a connection port 132. The inner cross-sectional shape of the connection port 132 is configured to approximately conform to the cross-sectional shape of the entry portal 112, while the outer cross-sectional shape of the connection port 132 is configured to engage with an in-line suction catheter 134. Typically, the in-line suction catheter 134 comprises a flexible, long tube 136 attached on a first end 138 to a suction valve 140. The suction valve 140 includes a suction port 142 that couples the in-line suction catheter 134 to a collection container and a device that generates suction (not shown). An opposing end 144 of the tube 136 is coupled to an elbow 146, where the elbow 146 includes a breathing tube (endotracheal or tracheostomy tube) port 148 and a ventilator port 150. Because the in-line suction catheter 134 is typically used with ventilated patients that are especially susceptible to infection, the tube 136 is enclosed in a sterile plastic sheath 152 to prevent the introduction of bacteria into the patient during suctioning. In the embodiment shown in FIG. 8, the suction port 142 of the in-line suction catheter 134 is coupled to the collection container and the device that generates suction (not shown). The breathing tube port 148 of the in-line suction catheter 134 is coupled to the connection port 132 of the insertion aid device 100, instead of a breathing tube. The ventilator port 150 that is typically connected to the ventilator remains uncoupled or capped when the in-line suction catheter 134 is used with the insertion aid device 100, as this port is not required for in-line suctioning with the insertion aid device 100. Likewise, an irrigation port 154, which typically is used to inject saline down the breathing tube to loosen secretions, is not required when using the in-line suction catheter 134 with the insertion aid device 100, but is required to irrigate and clean out debris from the in-line suction catheter 134 and the first passageway 106. The suction valve 140 is used to control when suctioning is being administered through the in-line suction catheter 134. As a result, the insertion aid device 100 is configured to retrofit with the existing components of the in-line suction catheter 134.

Figure 14:
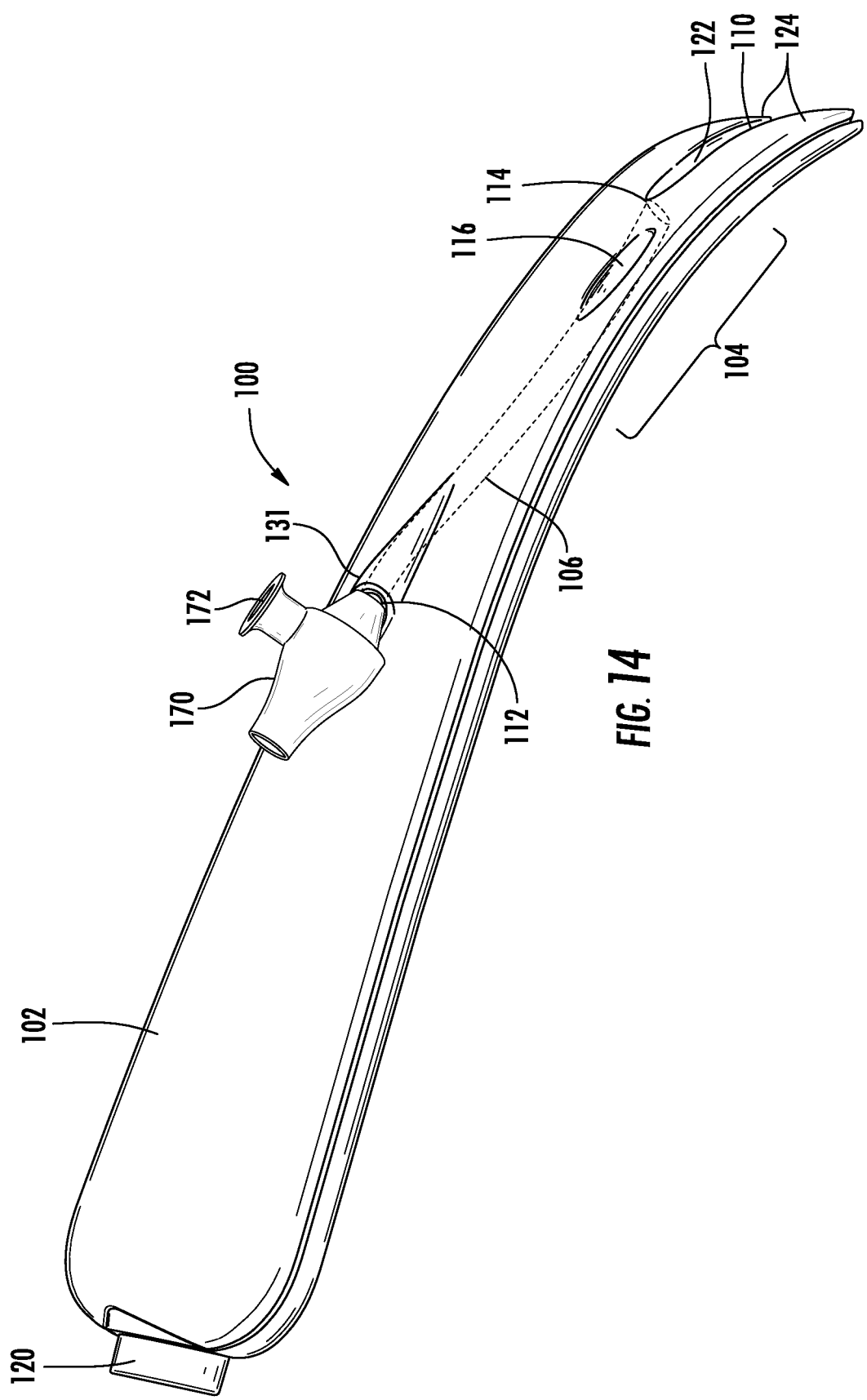
FIG. 14 is a perspective view of an insertion aid device according to another alternative embodiment of the present invention in use with a thumb port.

In another alternative embodiment shown in FIG. 14, the entry portal 112 of the first passageway 106 may be configured to couple with a thumb port 170 comprising a hole 172. The thumb port 170 may be configured to transform the first passageway 106 into a suctioning device itself.

Figure 18:
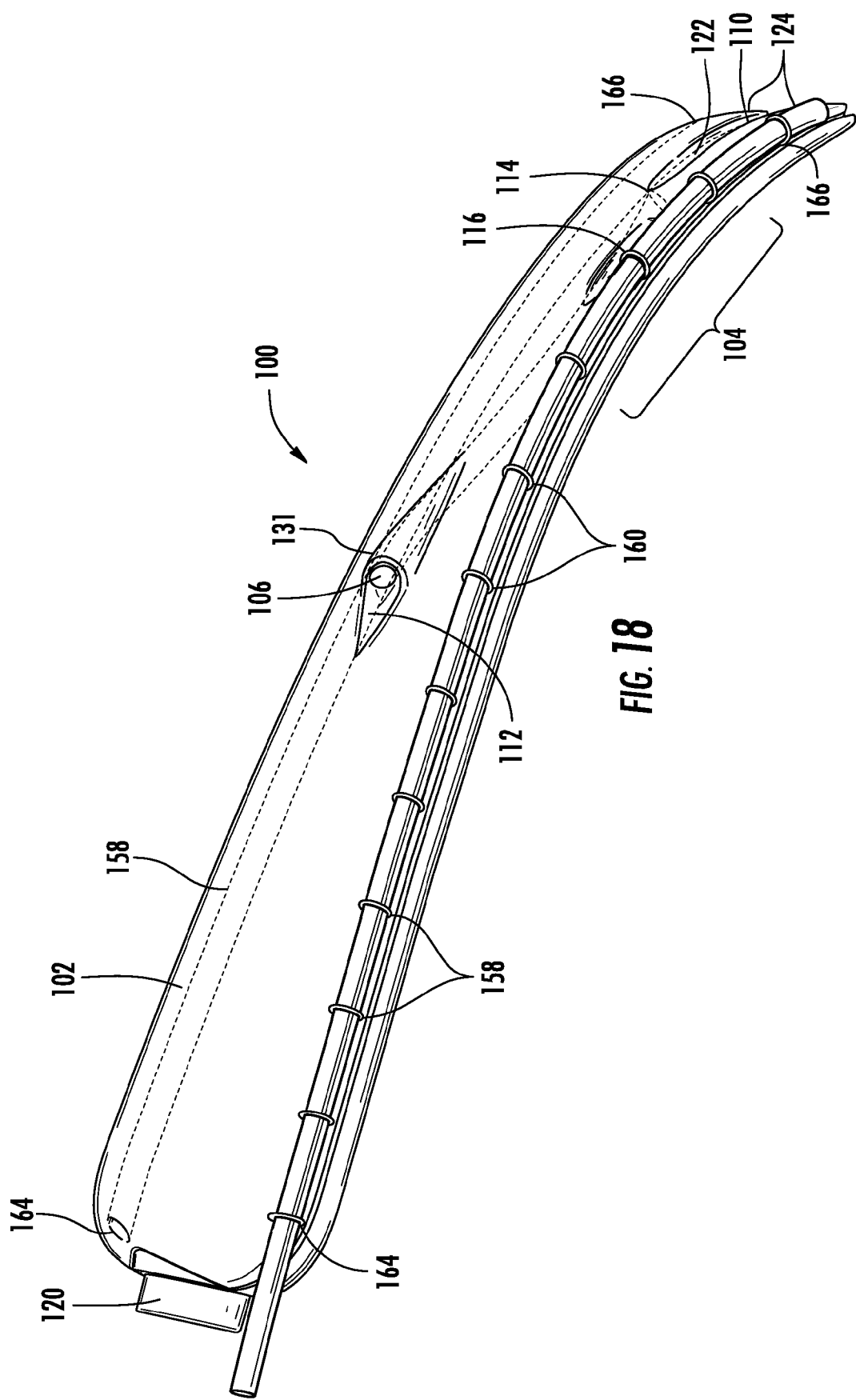
FIG. 18 is a perspective view of an insertion aid device according to another alternative embodiment of the present invention.
Figure 19:
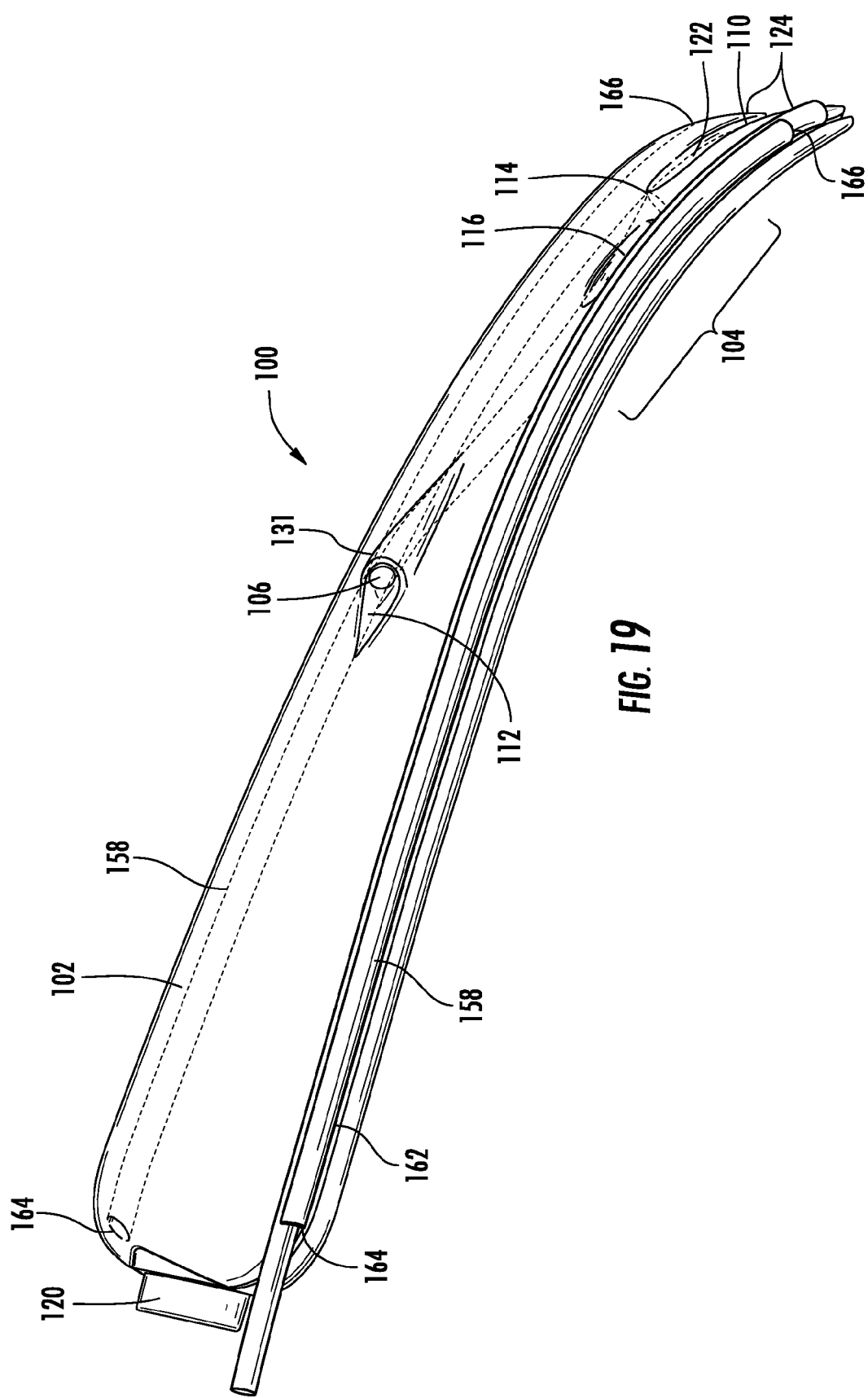
FIG. 19 is a perspective view of an insertion aid device according to another alternative embodiment of the present invention.

In other embodiments, such as those illustrated in FIGS. 9-13 and 18-19, the insertion aid device 100 further comprises at least one additional passageway 158. The cross-sectional size of the additional passageway 158 can be of various sizes, such as large bore or small bore, or other suitable sizes as needed. As shown in FIGS. 9-13 and 18-19, the additional passageway 158 is coupled to the tongue depressor 104 and positioned proximate at least a portion of the longitudinal axis of the insertion aid device 100. However, one of skill in the art will understand that any appropriate orientation of the additional passageway 158 may be used within the insertion aid device 100. Additionally, as illustrated in FIGS. 18 and 19, one of ordinary skill in the relevant art will understand that the insertion aid device 100 may comprise any number of additional passageways 158, so as to equip the insertion aid device 100 with two total passageways, three total passageways, and so on.

Figure 11:
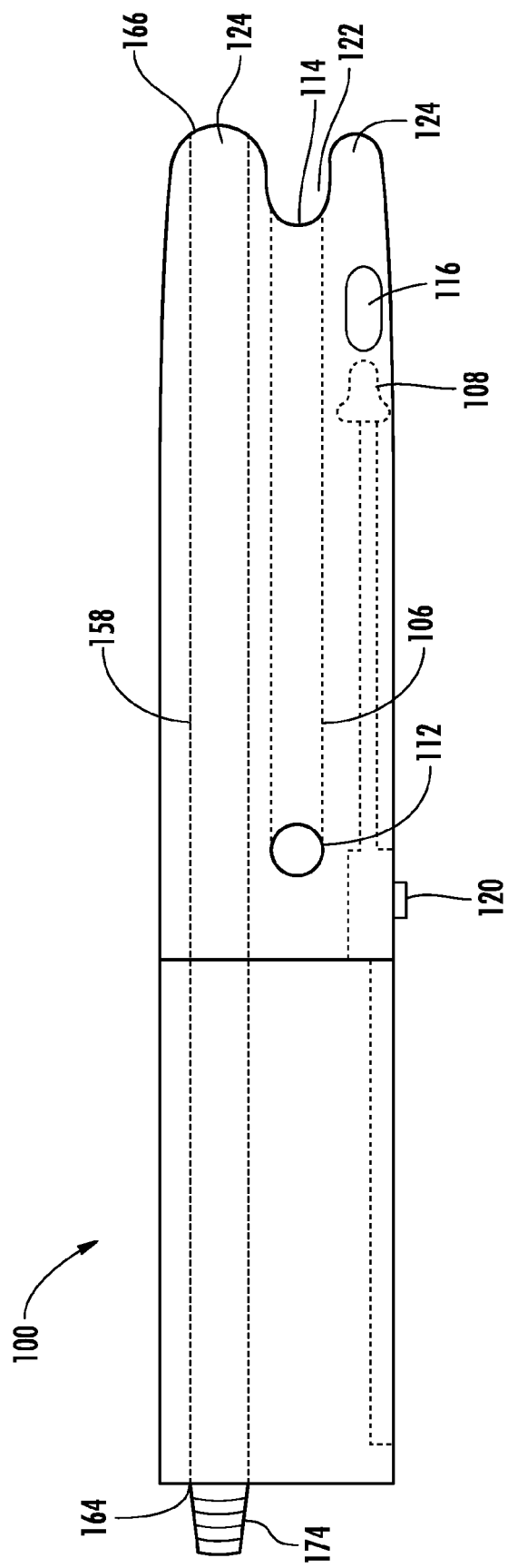
FIG. 11 is a top view of an insertion aid device according to another alternative embodiment of the present invention.
Figure 12:
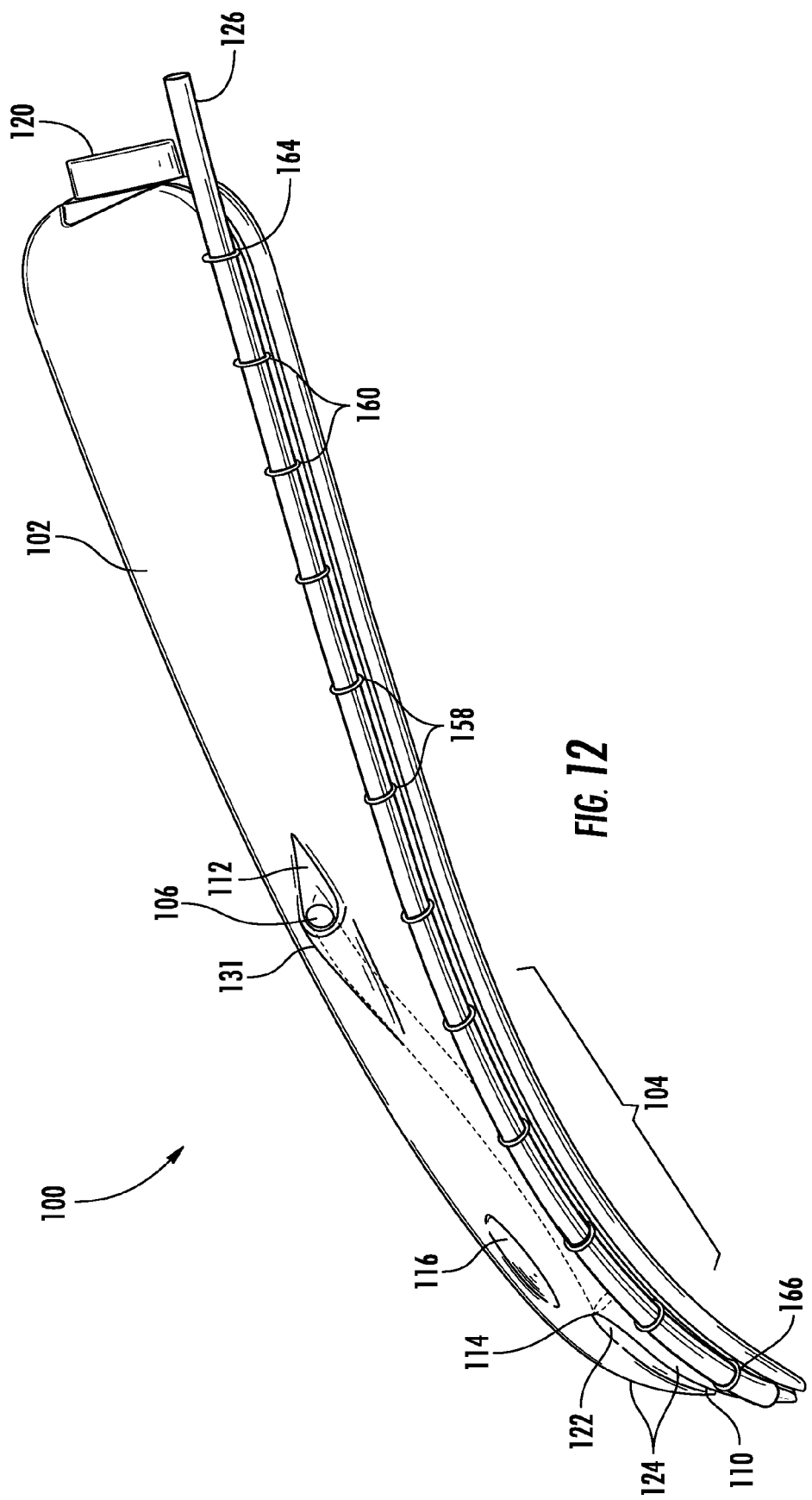
FIG. 12 is a perspective view of an insertion aid device according to another alternative embodiment of the present invention.
Figure 13:
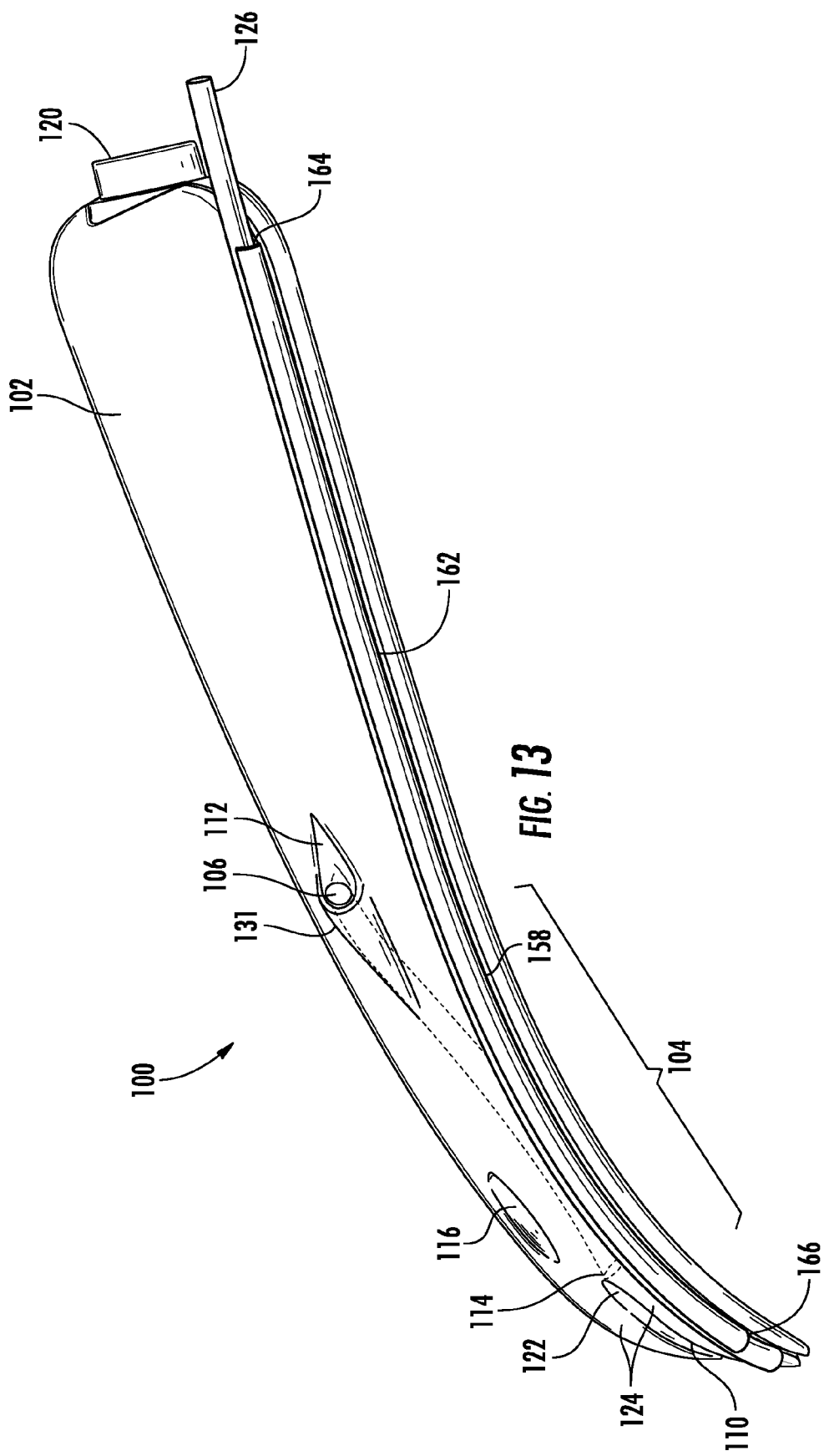
FIG. 13 is a perspective view of an insertion aid device according to another alternative embodiment of the present invention.

For example, in some embodiments, such as those illustrated in FIGS. 12-13, the additional passageway 158 may be proximate at least a portion of an external surface of the insertion aid device 100. In those embodiments, the additional passageway 158 may be formed alongside the insertion aid device 100 by a number of means, including but not limited to, a plurality of C-clips 160 or a shelf 162, or other suitable coupling mechanisms. In the embodiments illustrated in FIG. 12, for example, the additional passageway 158 is formed by the C-clips 160, which are attached to the external surface of the insertion aid device 100. A catheter, or other similar medical device, can be threaded through the C-clips 160 for use with the insertion aid device 100. A similar result in achieved in the embodiments illustrated in FIG. 13, in which the additional passageway 158 is formed by a shelf 162, which is attached to the external surface of the insertion aid device 100. In other embodiments, such as the embodiments illustrated in FIGS. 9-11, the additional passageway 158 is positioned substantially within the insertion aid device 100. In yet other embodiments containing multiple additional passageways 158, such as the embodiments illustrated in FIGS. 18 and 19, the additional passageways 158 may be positioned in a variety of locations.

Figure 9:
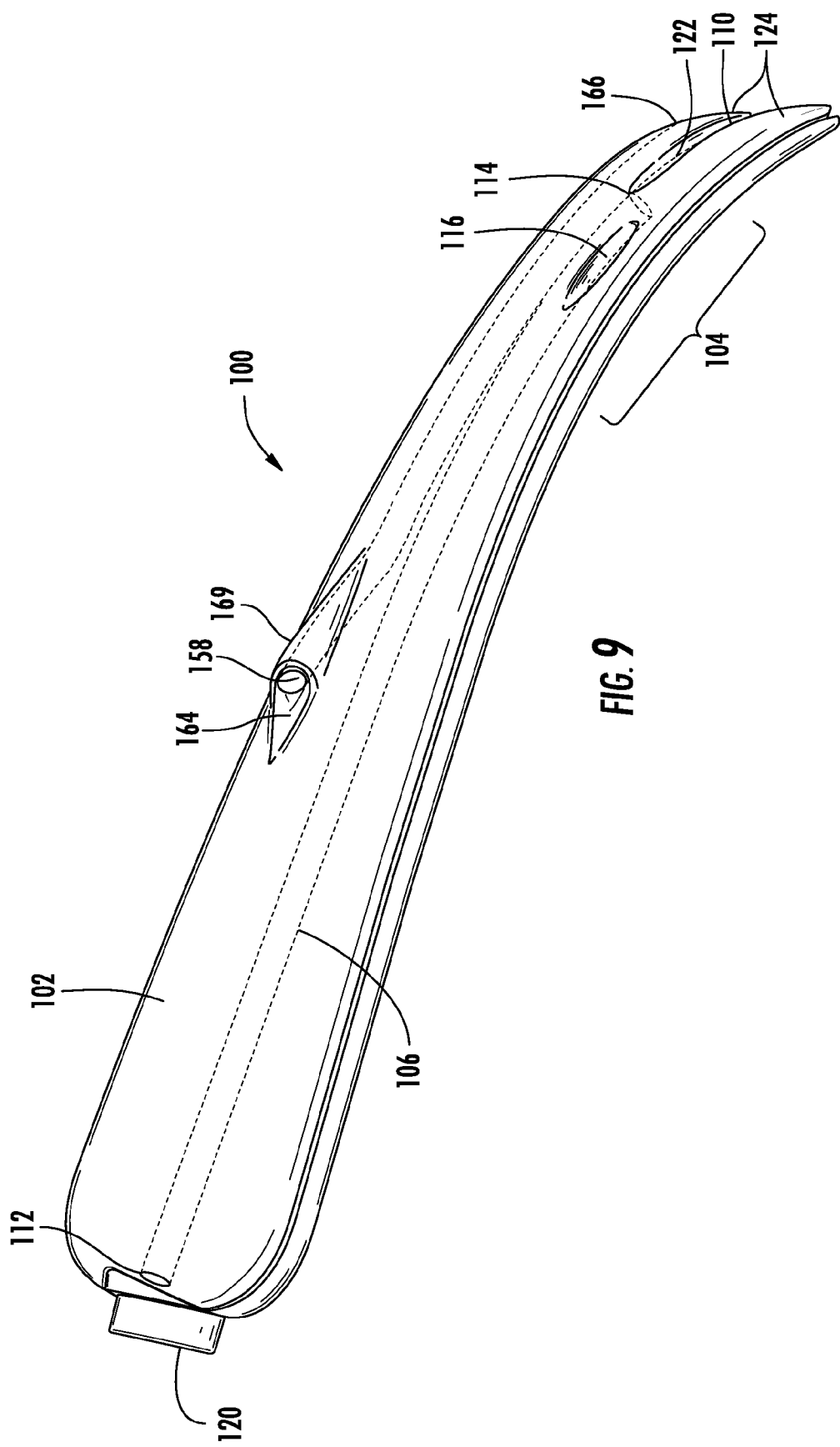
FIG. 9 is a perspective view of an insertion aid device according to another alternative embodiment of the present invention.
Figure 10:
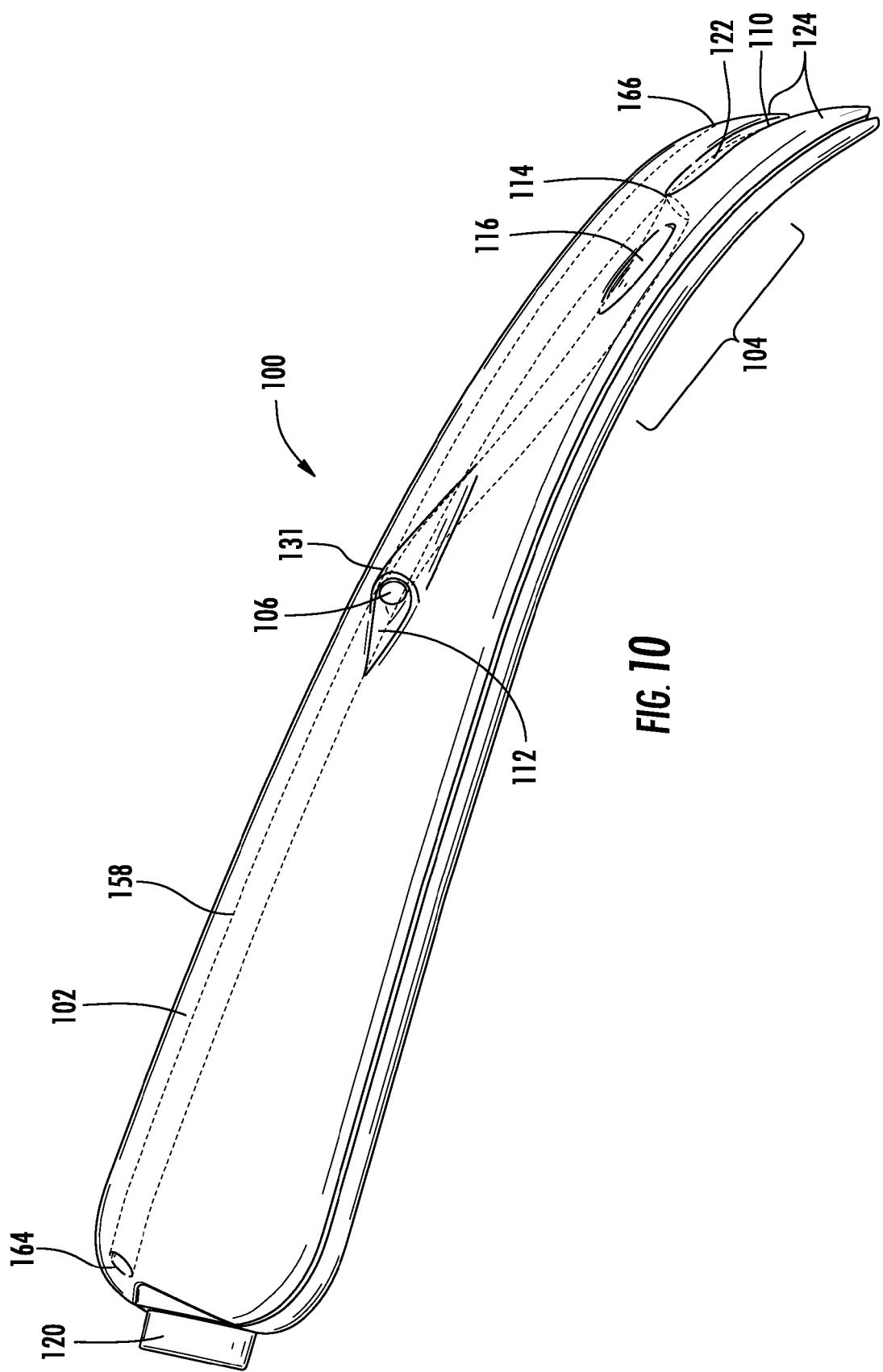
FIG. 10 is a perspective view of an insertion aid device according to another alternative embodiment of the present invention.

In some embodiments, such as the embodiment illustrated in FIG. 9, the additional passageway 158 includes an entry portal 164, which is located adjacent the proximal end of the tongue depressor 104. In other embodiments, such as illustrated in FIGS. 10-13 and 18-19, the entry portal 164 is located adjacent the handle 102. The additional passageway 158 includes an exit portal 166 adjacent the distal end of the tongue depressor 104. In some embodiments, the first passageway 106 and the additional passageway 158 may share an entry portal 112. Likewise, in some embodiments, the first passageway 106 and the additional passageway 158 may share an exit portal 114.

In some embodiments, the additional passageway 158 further includes at least one alternative entry portal 168, in addition to the entry portal 164. The alternative entry portal 168 allows the caregiver to access the additional passageway 158 from a location other than the entry portal 164. This additional access point may expedite the medical procedures performed by the caregiver and may be useful in instances in which a problem occurs with the entry portal 164, such as clogging, in where a saline flush or medication lavage can be used to flush out the clog. In some embodiments, the alternative entry portal 168 may be adjacent the handle 102. In other embodiments, the alternative entry portal 168 may be adjacent the proximal end of the tongue depressor 104.

In other embodiments, such as the embodiment illustrated in FIG. 9, the entry portal 164 includes an angled projection 169 to facilitate insertion of the tracheal suction catheter 126, or other similar device, by allowing the caregiver to insert the tracheal suction catheter 126, or other similar device, at an angle that is less than 90 degrees from the central axis of the handle 102.

In the embodiments illustrated in FIGS. 1-19, the light source 108 is coupled to the tongue depressor 104. An aperture 116 is formed in the tongue depressor 104 that allows light emitted from the light source 108 to pass through the tongue depressor 104. The light source 108 is coupled to a power source 118. In these embodiments, the power source 118 is positioned within the handle 102. However, one of skill in the relevant art will understand that the power source 118 may be positioned in any appropriate location either within or external to the insertion aid device 100. The power source 118 may include a battery or a power cord. In some embodiments, the handle 102 may include a rechargeable power source 118, where the handle 102 is placed on a battery charger between uses to re-charge the power source 118, and the tongue depressor 104 is removed from the handle 102 and disposed of after each use. In other embodiments, multiple light sources 108 may be coupled to the tongue depressor 104.

Figure 2:
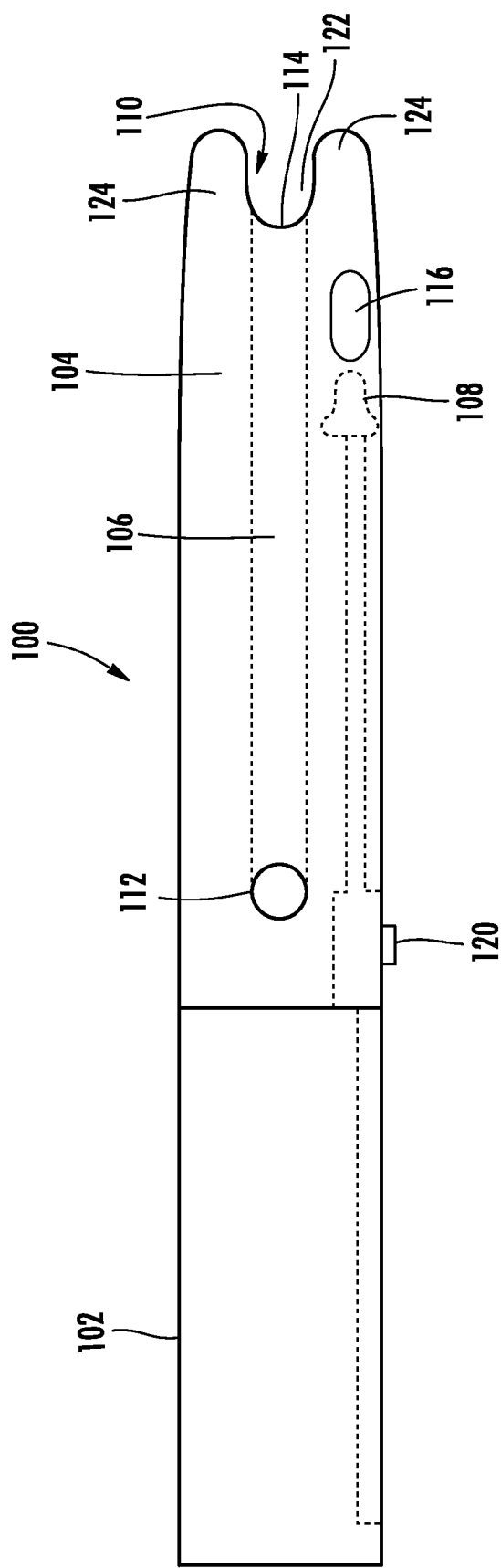
FIG. 2 is a top view of the insertion aid device of FIG. 1.

In the embodiment shown in FIGS. 1, 2, and 11, a switch 120 is located near the proximal end of the tongue depressor 104. In other embodiments, such as the embodiments illustrated in FIGS. 7-10 and 12-19, the switch 120 is positioned near the proximal end of the handle 102. In each of these embodiments, the operator of the insertion aid device 100 can activate the light source 108 by activating the switch 120. The light source 108 may be a conventional light bulb or a light emitting diode ("LED").

Figure 3:
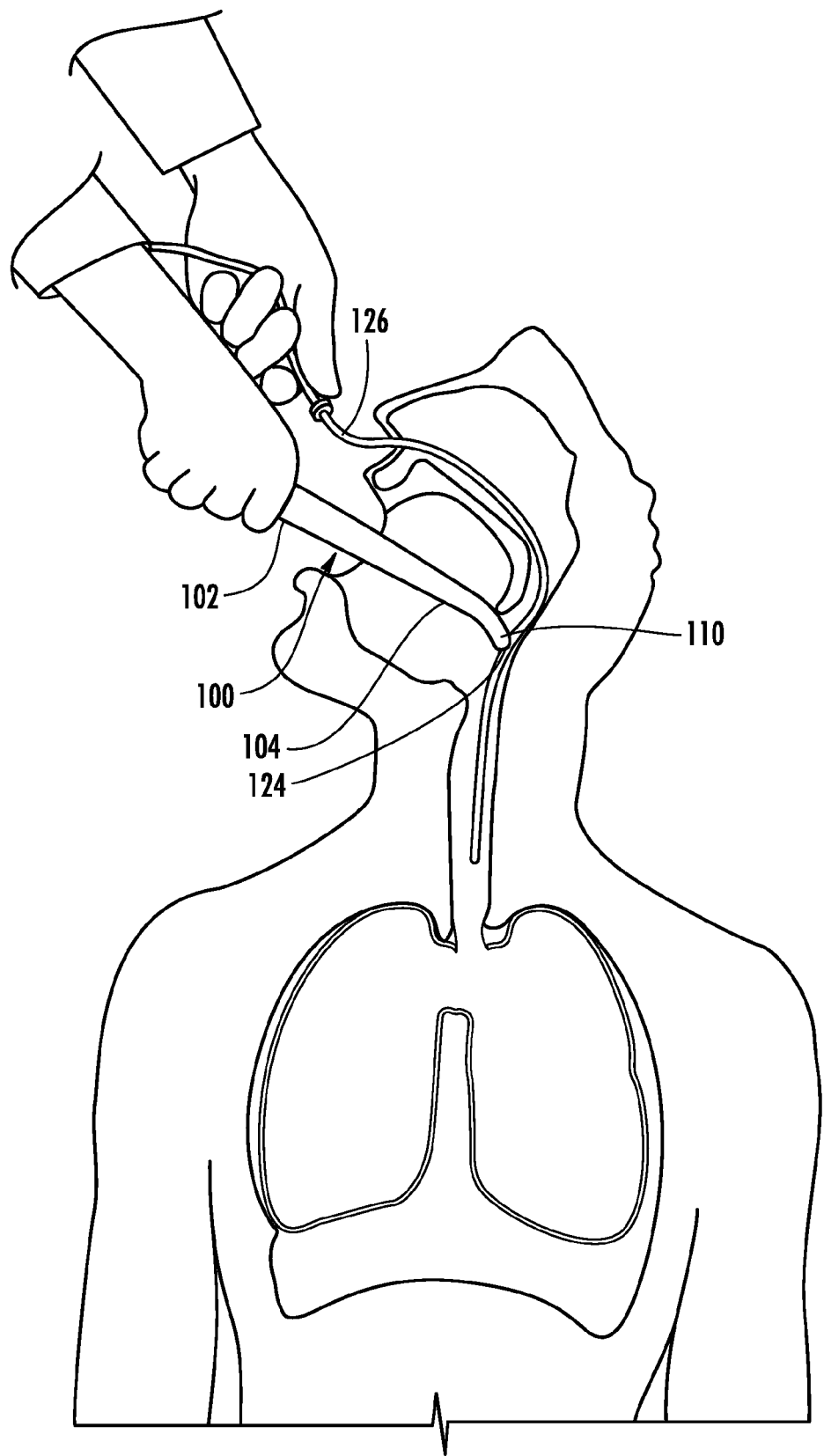
FIG. 3 is a side view of the insertion aid device of FIG. 1 in use with an nasotracheal suctioning procedure.
Figure 4:
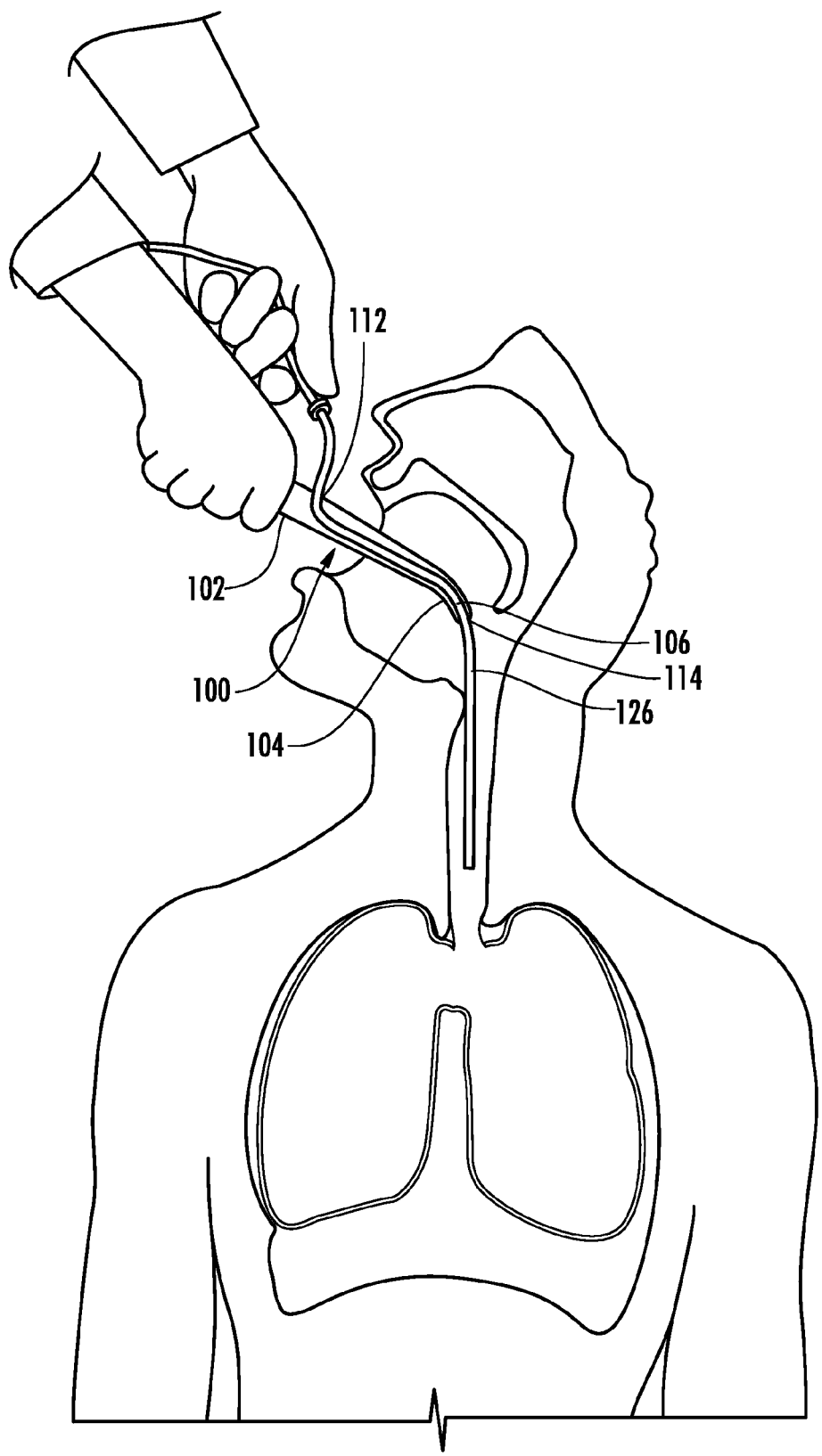
FIG. 4 is a side view of the insertion aid device of FIG. 1 in use with an orotracheal suctioning procedure.
Figure 5:
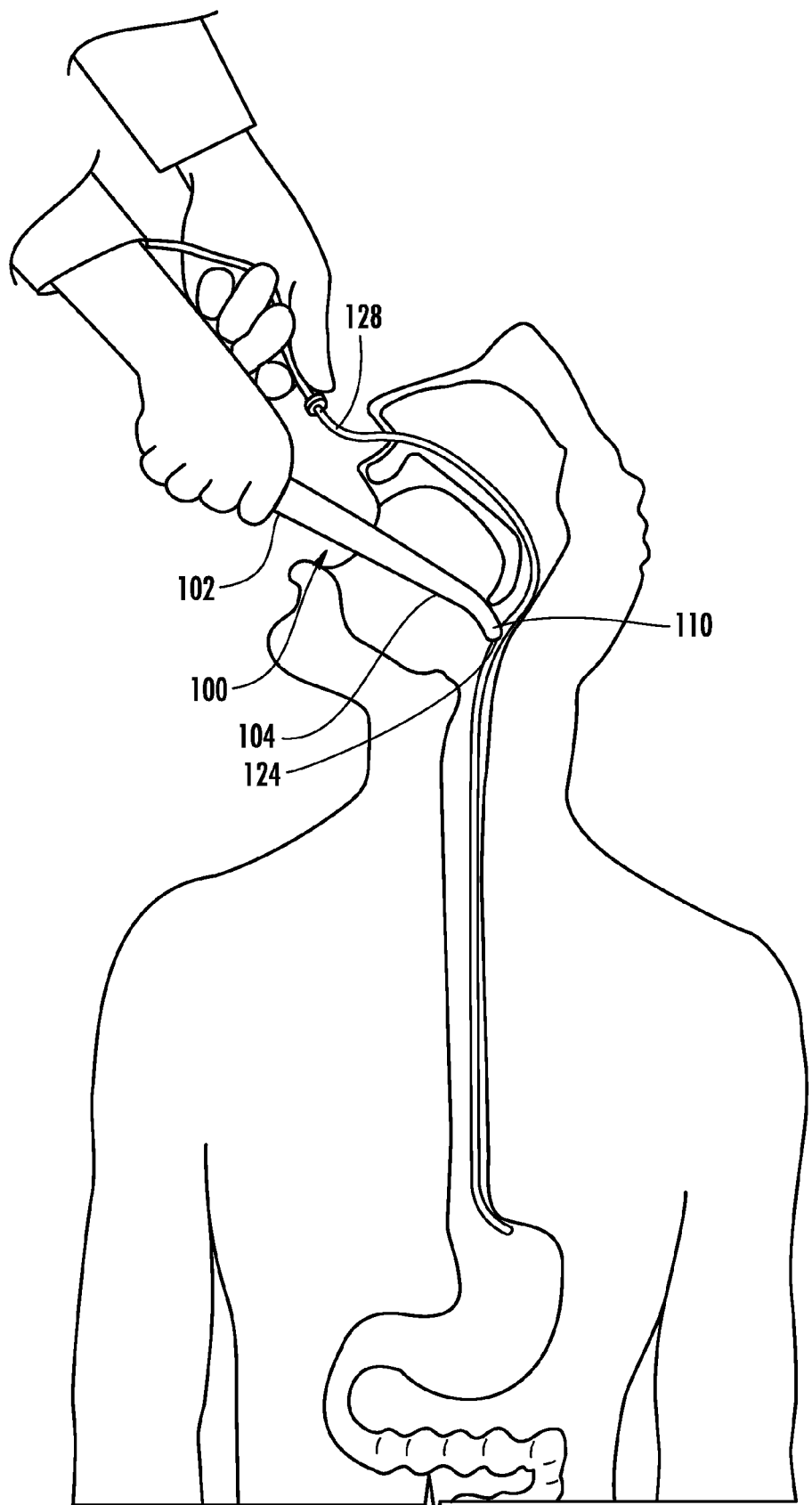
FIG. 5 is a side view of the insertion aid device of FIG. 1 in use with a nasogastric tube insertion procedure.
Figure 6:
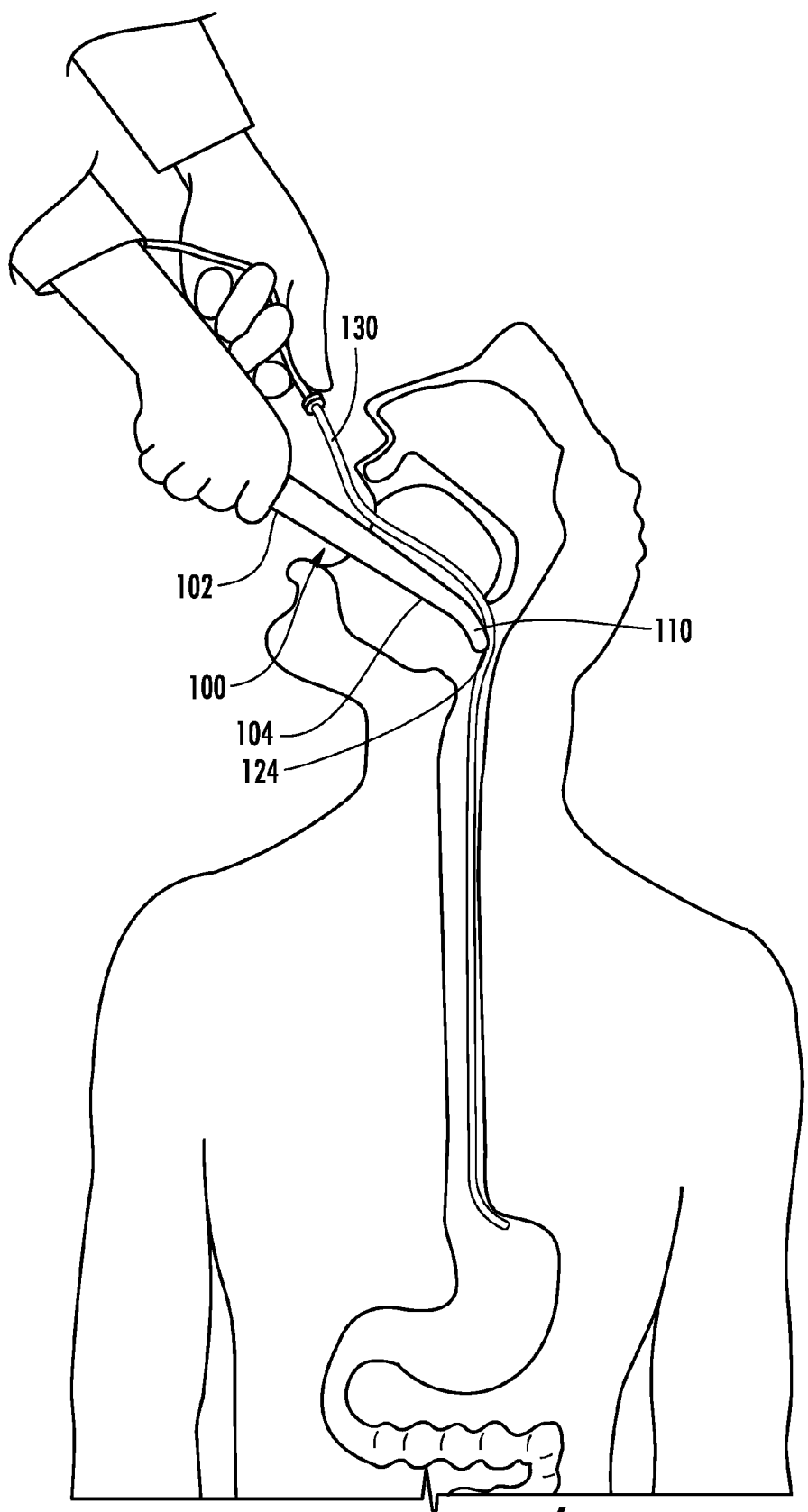
FIG. 6 is a side view of the insertion aid device of FIG. 1 in use with an orogastric tube insertion procedure.
Figure 7:
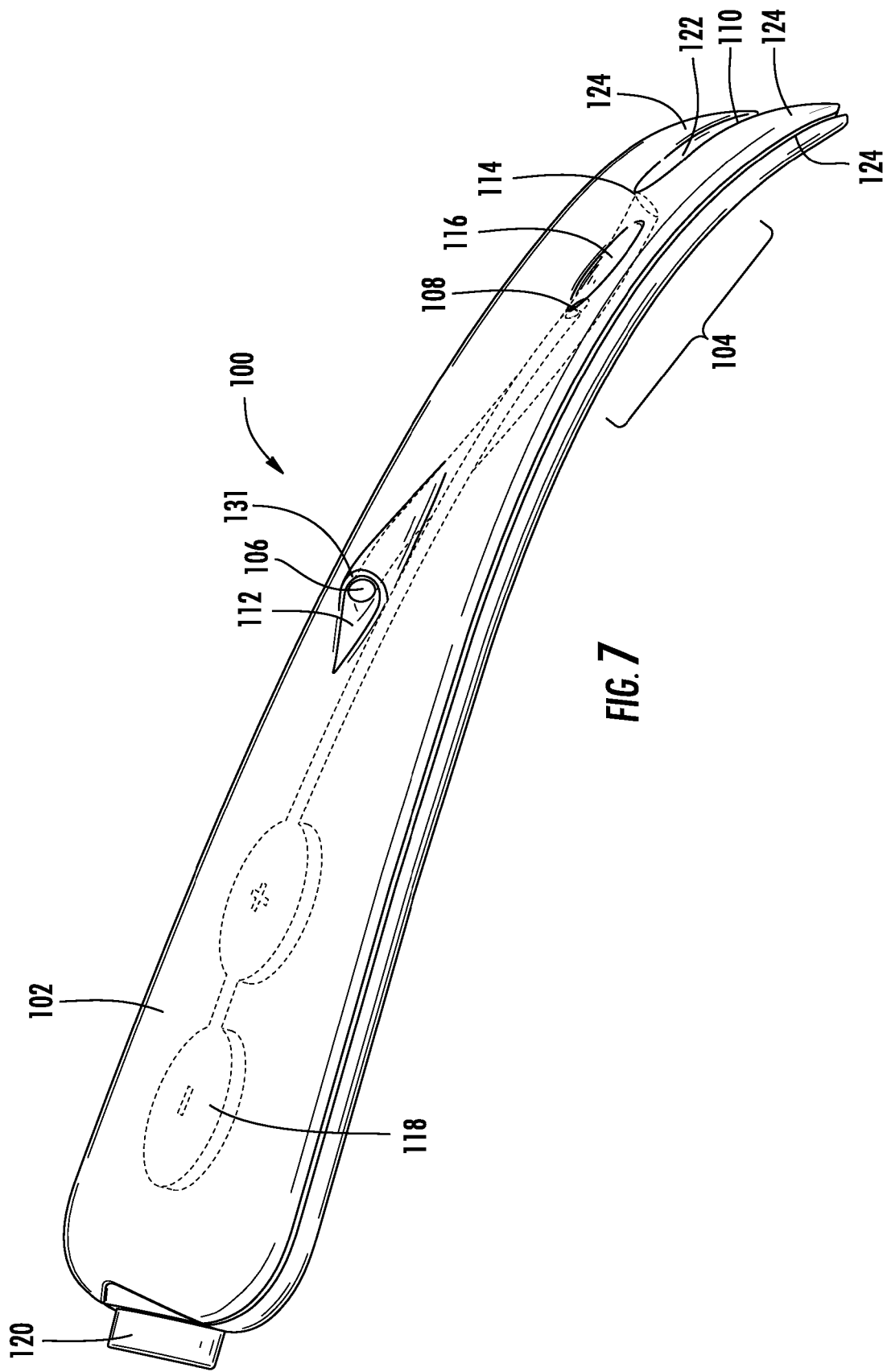
FIG. 7 is a perspective view of an insertion aid device according to an alternative embodiment of the present invention.

In the embodiments shown in FIGS. 1-19, the guide 110 is positioned at the distal end of the tongue depressor 104. In some embodiments, the guide 110 is integrally formed with the tongue depressor 104. In other embodiments, the guide 110 is coupled to the tongue depressor 104 and may be formed of the same or different materials than the tongue depressor 104. For example, in some embodiments, the guide 110 may be constructed from rigid material such as plastic, steel, or any other suitable material, while the tongue depressor 104 is formed of similar or other materials. In other embodiments, the guide 110 is constructed of a flexible material such as rubber or soft plastic, while the tongue depressor 104 is formed of similar or other materials. In yet other embodiments, the guide 110 is constructed from rigid material such as plastic, steel, or any other suitable material, which is then covered with soft rubber or a silicone overmold. As best illustrated in FIGS. 2, 7, 8, and 11, the guide 110 has a recess 122 formed by two prongs 124 that extend along each side of the exit portal 114. The recess 122 is shaped to accommodate the cross-sectional shape of a tracheal suction catheter 126 (as shown in FIGS. 3 and 4), a nasogastric tube 128 (as shown in FIG. 5), or an orogastric tube 130 (as shown in FIG. 6).

In some embodiments, such as those illustrated in FIGS. 2 and 7-10, the two prongs 124 are of proportionate shape and size. In other embodiments, such as the embodiment illustrated in FIG. 11, the two prongs 124 may be dissimilar or non-proportionate in shape and/or size. In those embodiments, one prong 124 may be wider than the other prong 124. This difference may be seen in embodiments where the insertion aid device 100 comprises one or more additional passageways 158. In these embodiments, for example, the exit portal(s) 166 of the one or more additional passageway 158 may be adjacent the wider prong 124.

The length of the insertion aid device 100 may vary in accordance with the dimensions of the mouth of the patient. For example, the insertion aid device 100 may be used with a variety of patients ranging in age from infant to adult and having a range of sizes of mouth or oral cavities. Because the insertion aid device 100 may be used with a range of mouth or oral cavities, the insertion aid device 100 may be manufactured in a plurality of sizes, wherein each size is configured to fit a particular sized mouth or oral cavity. Typically, the insertion aid device 100 may be between approximately 6 inches long and 12 inches long and the circumference may be between approximately 1 inch and 3 inches. The length of the handle 102 may be between approximately 3 inches and 4 inches. However, one of skill in the relevant art will understand that any suitable length may be used that will accomplish the desired task without risk of injury to the patient or the caregiver. In some alternative embodiments (not shown), the insertion aid device 100 may include a telescoping design that allows the length of the insertion aid device 100 to be adjusted as needed.

Figure 15:
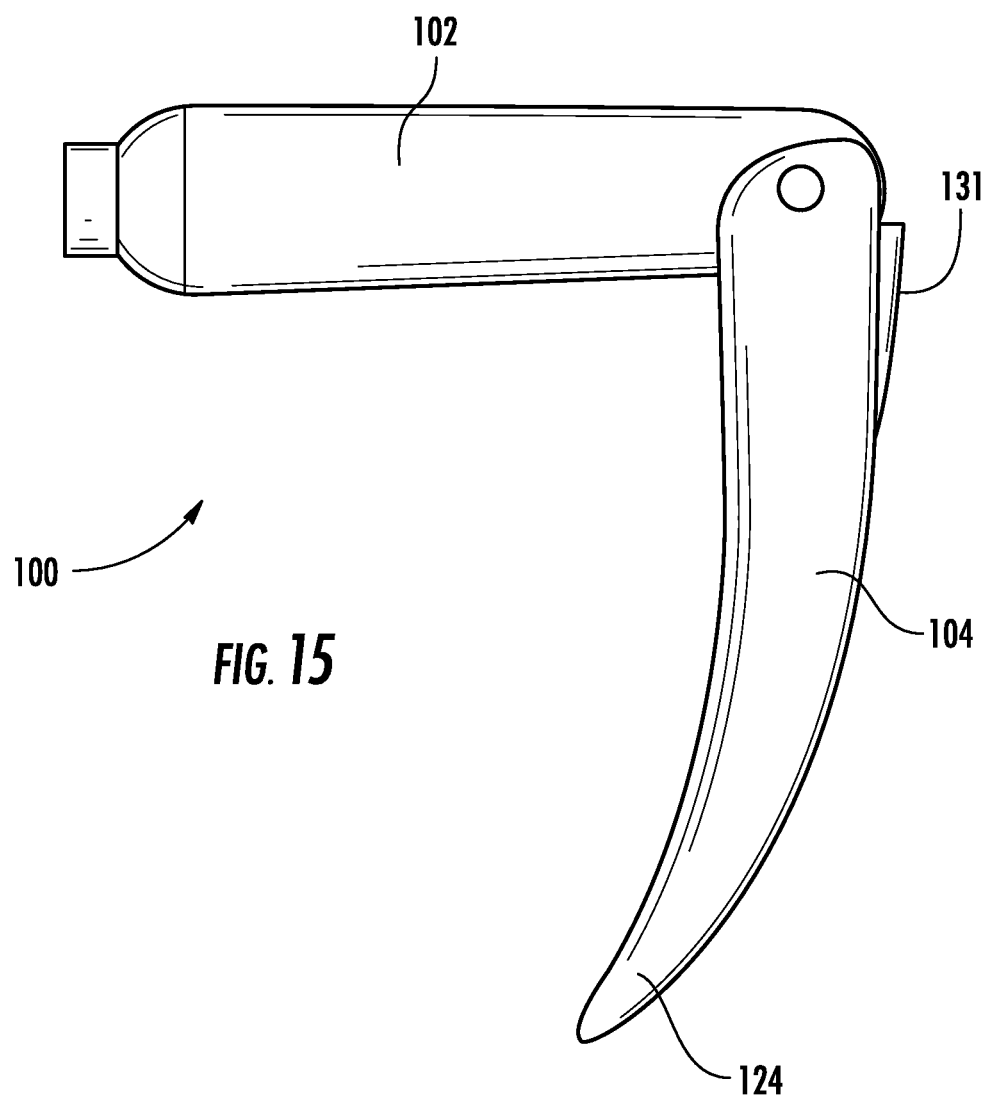
FIG. 15 is a side view of an insertion aid device according to another alternative embodiment of the present invention.
Figure 16:
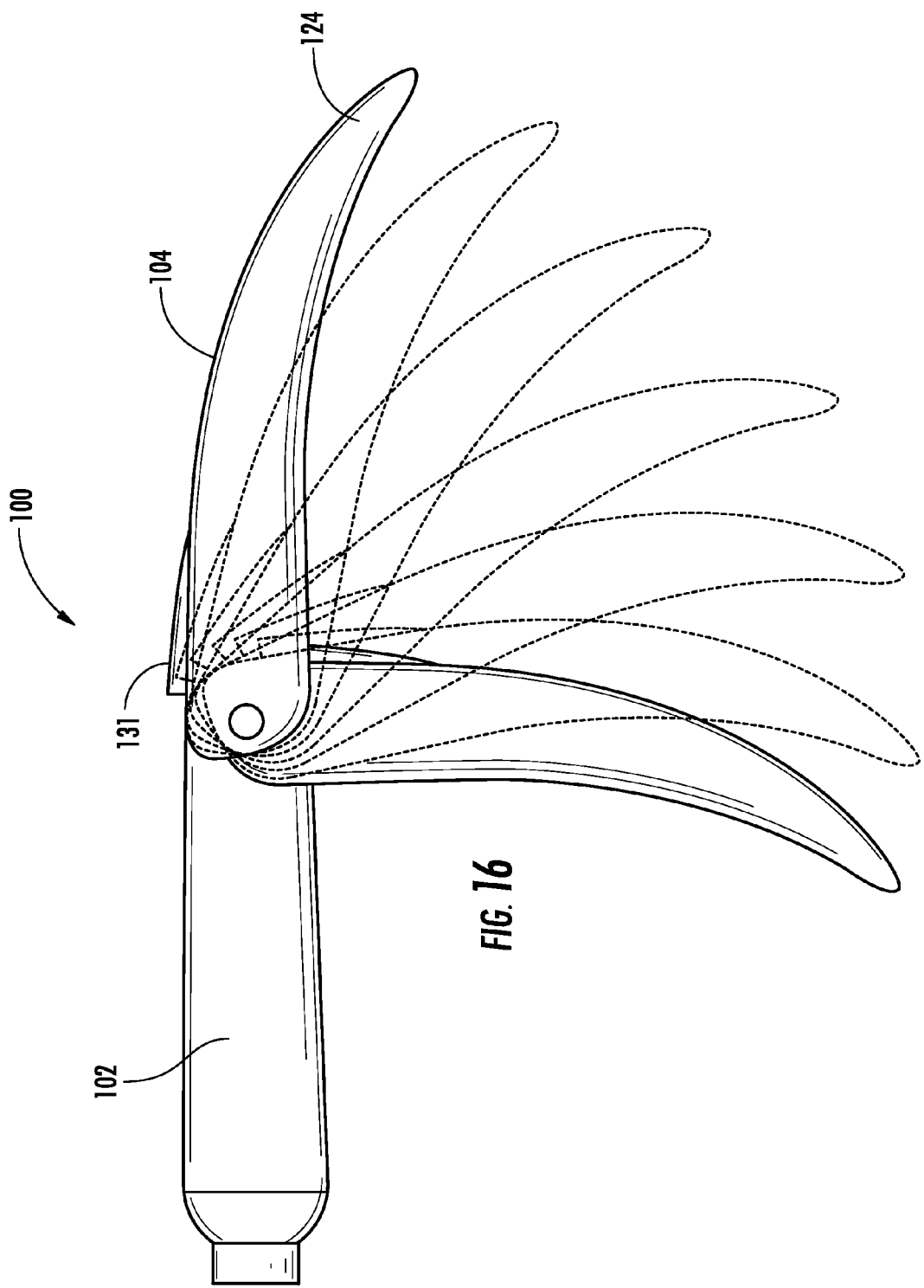
FIG. 16 is a side view of the insertion aid device of FIG. 15.
Figure 17:
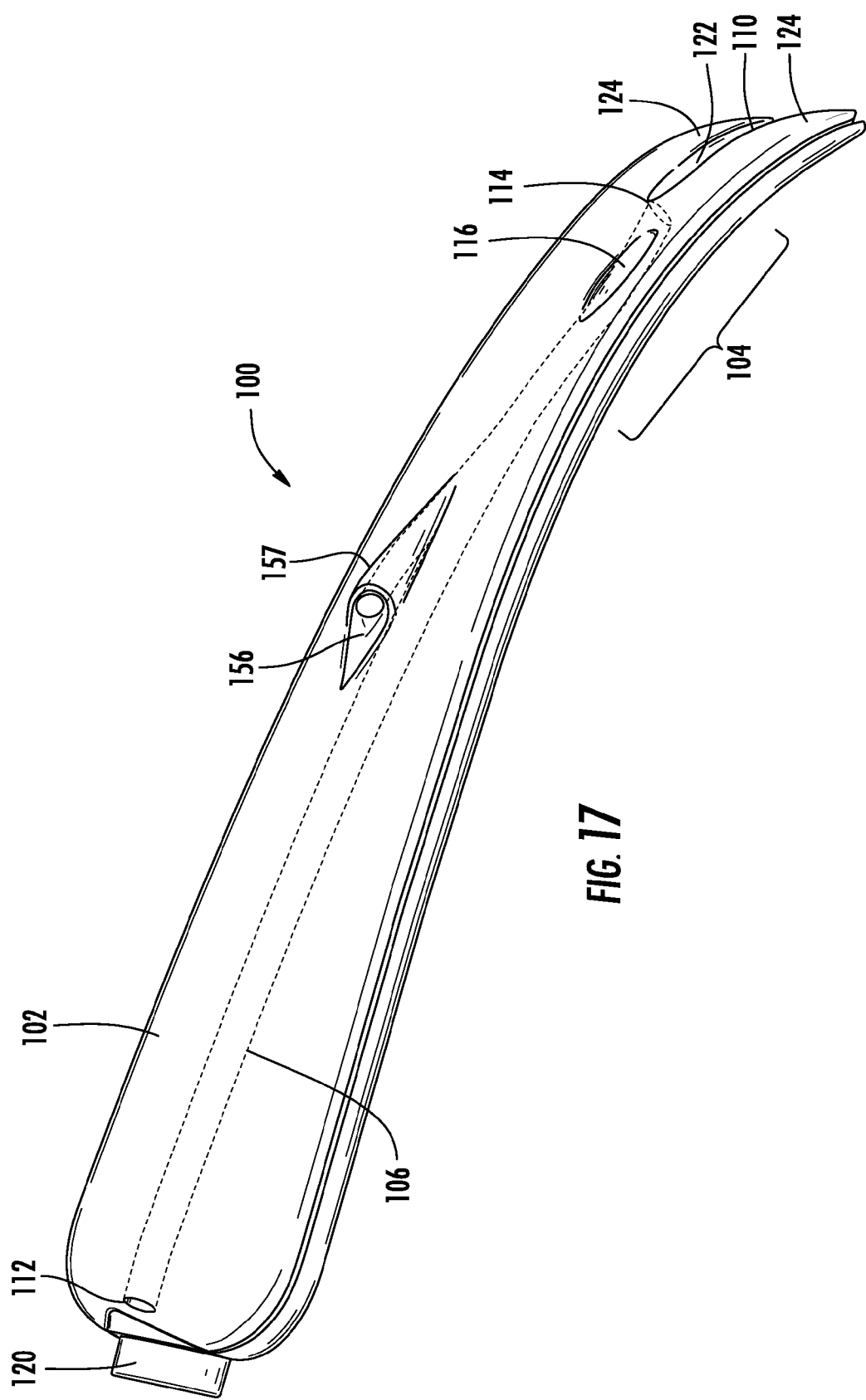
FIG. 17 is a perspective view of an insertion aid device according to another alternative embodiment of the present invention.

Additionally, in embodiments in which the tongue depressor 104 is coupled to the handle 102, such as the embodiment illustrated in FIGS. 15 and 16, the insertion aid device 100 may be configured for use as a laryngoscope or other suitable application. In these embodiments, the tongue depressor 104 is pivotally coupled to the handle 102 such that it may rotate within the plane of the handle 102, while the proximal end of the tongue depressor 104 remains coupled to the distal end of the handle 102. As illustrated in FIGS. 15 and 16, the tongue depressor 104 may rotate relative to the handle 102 over a range of positions, whereby it may be used in connection with the handle 102 as a laryngoscope. The tongue depressor 104 may be coupled to the handle 102 such that it may be held in position once the desired position is reached.

In these embodiments, the tongue depressor 104 may be pivotally coupled and/or held in position relative to the handle 102 by a variety of mechanisms, including but not limited to mechanical fasteners, snap-fit, or other suitable rotations and/or releasable fastening devices.

The pivotally coupled relationship of the tongue depressor 104 and the handle 102 provides additional versatility to the insertion aid device 100. For example, a patient requiring tracheal suctioning is usually in a weakened state and at risk of being intubated and put on a ventilator. Due to variety of patients' anatomies, the insertion aid device 100 may need to be shaped at an angle, such as 45 degrees, to achieve a sufficient approach for efficient tracheal suctioning. Successful tracheal suctioning with the insertion aid device 100 at such an angle may, when paired with BiPAP or CPAP therapy, prevent an intubation. If a patient's condition continues to decline, however, and perhaps progress into respiratory distress, the insertion aid device 100 may be snapped or shaped into a further-angled position, such as a 90 degree position, thereby becoming a laryngoscope, to intubate the patient.

In other situations where a patient in found unconscious in the field, emergency room, ambulance, or other locations, the patient may be in respiratory arrest with a large amount of emisis in the mouth and throat. In these situations, the insertion aid device 100 may be snapped or shaped into a further-angled position, such as a 90 degree position, thereby becoming a laryngoscope, to intubate the patient.

In each of these situations, as well as many other similar examples, the ability of the insertion aid device 100 to be manipulated in such a manner increases the caregiver's ability to respond to a patient's condition, where every second matters.

Throughout embodiments, the tongue depressor 104 may have various shapes and sizes. The shape and size of the tongue depressor 104 may vary depending on the specific application. However, one of skill in the relevant art will understand that the tongue depressor 104 may have any appropriate shape that allows a caregiver to use the insertion aid device 100 to accomplish the desired task without risk of injury to the patient or the caregiver. For example, in some embodiments, the shape and size of the tongue depressor 104 may resemble a Macintosh blade. In other embodiments, the shape and size of the tongue depressor 104 may resemble a Miller blade. In yet other embodiments, the shape and size of the tongue depressor 104 may resemble the shape and size of other traditional commercial blades.

In use, the insertion aid device 100 performs several functions. Specifically, the insertion aid device 100 is designed to improve oral suctioning and cleaning, nasal and oral tracheal suctioning, and insertion of nasal and oral gastric tubes, feeding tubes, and other medical devices, including but not limited to a sinus scope, biopsy tool, or a fiberoptic scope.

When performing oral suctioning and cleaning, nasotracheal suctioning, orotracheal suctioning, and orogastric tube insertion, a caregiver begins each process by inserting the insertion aid device 100 into the patient's mouth. The tongue depressor 104 is placed in contact with the lower portion of the patient's mouth and tongue. The shape of the tongue depressor 104 depresses the tongue and maintains the patient's mouth in an open position, preventing the patient from fighting the caregiver and providing improved viewing of the oral cavity. Once the insertion aid device 100 has been inserted, the caregiver may turn on the light source 108 for further improvement in oral cavity viewing. With the patient's mouth now held in an open position by the insertion aid device 100, the caregiver may proceed to perform the specific steps associated with each of these processes.

For example, the caregiver proceeds to perform oral cleaning with a foam swab and various antiseptic solutions and/or oral suctioning without risk of the patient biting down on the swab or suctioning device.

To perform nasotracheal suctioning, as shown in FIG. 3, the caregiver inserts the tracheal suction catheter 126 into the patient's narias. Once the tube is visible in the back of the mouth, the caregiver then engages the guide 110 with the tracheal suction catheter 126 to position the tracheal suction catheter 126 into the trachea until the desired depth of the trachea is reached to suction unwanted secretions out. The guide 110 prevents the tracheal suction catheter 126 from coiling in the back of the throat and decreases the chances of triggering the patient's gag reflex.

To perform orotracheal suctioning, as shown in FIG. 4, the caregiver inserts the tracheal suction catheter 126 into the first passageway 106 until the desired depth of the trachea is reached to suction unwanted secretions out. The tongue depressor 104 prevents the patient from biting down on the tracheal suction catheter 126. The first passageway 106 prevents the tracheal suction catheter 126 from coiling in the back of the throat and decreases the chances of triggering the patient's gag reflex. Furthermore, the first passageway 106 prevents the introduction of bacteria into the oral cavity and consequently prevents the introduction of bacteria into the lungs, decreasing the risk of infection.

To perform orogastric tube insertion, as shown in FIG. 6, the caregiver inserts the orogastric tube 130 into the patient's mouth. Once the tube reaches the back of the patient's mouth, the caregiver then engages the guide 110 with the orogastric tube 130 to position the orogastric tube 130 down the throat and into the stomach. The tongue depressor 104 prevents the patient from biting down on the orogastric tube 130. The guide 110 prevents the orogastric tube 130 from coiling in the back of the throat and decreases the chances of triggering the patient's gag reflex.

To perform nasogastric tube insertion, the caregiver begins by inserting the nasogastric tube 128 into the patient's narias and down into the throat. In the event the nasogastric tube 128 coils in the back of the patient's mouth, the caregiver inserts the insertion aid device 100 into the patient's mouth as described above. Once the insertion aid device 100 has been inserted, the caregiver may turn on the light source 108 for further improvement in oral cavity viewing. With the patient's mouth now held in an open position by the insertion aid device 100, the caregiver retracts the nasogastric tube 128 until the caregiver can see the tip of the nasogastric tube 128 in the back of the patient's mouth. As shown in FIG. 5, once the tube is visible in the back of the patient's mouth, the caregiver then engages the guide 110 with the nasogastric tube 128 to position the nasogastric tube 128 down the throat and into the stomach. The guide 110 prevents the nasogastric tube 128 from coiling in the back of the throat and decreases the chances of triggering the patient's gag reflex.

In the embodiments including the additional passageway 158, the additional passageway 158 may also be employed to assist in the above procedures, as well as providing flexibility to perform additional procedures.

For example, a more direct and therefore less-contaminated respiratory/sputum culture may be obtained through a method that utilizes the additional passageway 158 of the insertion aid device 100. In such a method, the first passageway 106 is utilized to perform oral suctioning, while the additional passageway 158 is utilized to perform tracheal suctioning. The caregiver inserts the tracheal suction catheter 126 into the additional passageway 158 until the desired depth of the trachea is reached to suction unwanted secretions out. The tongue depressor 104 prevents the patient from biting down on the tracheal suction catheter 126. The additional passageway 158 prevents the tracheal suction catheter 126 from coiling in the back of the throat and decreases the chances of triggering the patient's gag reflex. Furthermore, the additional passageway 158 prevents the introduction of bacteria into the oral cavity and consequently prevents the introduction of bacteria into the lungs, decreasing the risk of infection. The caregiver then performs oral suctioning via the first passageway 106. At the conclusion of the oral suctioning, the caregiver can immediately perform the tracheal suctioning via the additional passageway 158 to obtain a more direct and less contaminated culture. In other methods, the first passageway 106 may be utilized for tracheal suctioning, while the additional passageway 158 may be utilized for oral suctioning.

The caregiver may perform the oral suctioning, among other means, by connecting the first passageway 106 to a wall or portable suction hose. This connection can be achieved and controlled by the thumb port 170, as illustrated in FIG. 14. The caregiver can perform the oral suctioning by covering the hole 172 of the thumb port 170, thereby turning the first passageway 106 into a suctioning device itself. The caregiver may then perform the tracheal suctioning after removing his or her thumb from the hole 172 and activating the tracheal suction catheter 126.

In yet other methods, saline, as administered via either the first passageway 106 or additional passageway 158, can also be used to lavage and stimulate cough before sputum collection. Aerosols or emergency liquid medicines can also be squirted though either the first passageway 106 or additional passageway 158 during a cardiac or respiratory arrest.

The additional passageway 158 also becomes useful in certain procedures if the first passageway 106 becomes clogged. For example, if the first passageway 106, or the catheter utilizing the first passageway 106, becomes clogged with vomit or otherwise during orotracheal suctioning, the caregiver may employ the additional passageway 158 to suction the substance contributing to the clogging or to otherwise complete the procedure.

The additional passageway 158 also allows caregivers the opportunity to perform additional medical procedures via the insertion aid device 100. For example, in addition to the procedures listed above utilizing only the first passageway 106, the additional passageway 158 allows caregivers to insert sinus scopes, biopsy tools, fiberoptic scopes, or cameras into the patient through the patient's throat. Additionally, in some embodiments, as illustrated in FIG. 11, a connection port 174 may be coupled to the entry portal 164 of the additional passageway 158 for connection of the additional passageway 158 to a wall suction hose or portable suction hose, thereby making the additional passageway 158 a suctioning device, like a Yankauer. The additional passageway 158 may also be utilized to insert Endotracheal Tubes or large-bore suction devices into the patient.

The foregoing is provided for purposes of illustrating, explaining, and describing embodiments of the present invention. Further modifications and adaptations to these embodiments will be apparent to those skilled in the art. The features and aspects of the present invention have been described or depicted by way of example only and are therefore not intended to be interpreted as required or essential elements of the invention unless otherwise so stated. It should be understood, therefore, that the foregoing relates only to certain exemplary embodiments of the invention, and that numerous changes and additions may be made thereto without departing from the spirit and scope of the invention as defined by any appended claims.

That which is claimed is:

1. An insertion aid device comprising:
   (a) a handle comprising a distal end;
   (b) a tongue depressor comprising:
      (i) a proximal end pivotally coupled to the distal end of the handle, wherein the tongue depressor is configured to be positioned between 0 degrees and 45 degrees relative to the handle during use; and
      (ii) a distal end, wherein the tongue depressor has a progressively smaller cross-sectional shape from the proximal end to the distal end;
   (c) a first passageway comprising:
      (i) an entry portal; and
      (ii) an exit portal adjacent the distal end of the tongue depressor;
   (d) at least one additional passageway comprising:
      (i) an entry portal; and
      (ii) an exit portal adjacent the distal end of the tongue depressor; and
   (e) a guide adjacent the distal end of the tongue depressor, wherein the guide comprises a recess formed by a pair of prongs that extend from the distal end of the tongue depressor.

2. The insertion aid device of claim 1, wherein the entry portal of the first passageway is positioned adjacent the proximal end of the tongue depressor.

3. The insertion aid device of claim 1, wherein the entry portal of the first passageway is positioned adjacent the handle.

4. The insertion aid device of claim 1, wherein the first passageway further comprises at least one alternative entry portal.

5. The insertion aid device of claim 1, wherein the entry portal of the at least one additional passageway is positioned adjacent the proximal end of the tongue depressor.

6. The insertion aid device of claim 1, wherein the entry portal of the at least one additional passageway is positioned adjacent the handle.

7. The insertion aid device of claim 1, wherein the at least one additional passageway is formed by a plurality of C-clips coupled to an external surface of the insertion aid device.

8. The insertion aid device of claim 1, wherein the at least one additional passageway is formed by a shelf coupled to an external surface of the insertion aid device.

9. An insertion aid device comprising:
   (a) a handle comprising a distal end;
   (b) a tongue depressor comprising:
      (i) a proximal end pivotally coupled to the distal end of the handle, wherein the tongue depressor is configured to be secured to the handle at a 0 degree position and a 45 degree position relative to the handle during use; and
      (ii) a distal end, wherein the tongue depressor has a progressively smaller cross-sectional shape from the proximal end to the distal end;
   (c) a first passageway comprising:
      (i) an entry portal;
      (ii) at least one alternative entry portal; and
      (iii) an exit portal adjacent the distal end of the tongue depressor; and
   (d) a guide adjacent the distal end of the tongue depressor, wherein the guide comprises a recess formed by a pair of prongs that extend from the distal end of the tongue depressor, wherein the exit portal is adjacent the recess.

10. The insertion aid device of claim 9, wherein the entry portal is adjacent the handle.

11. The insertion aid device of claim 9, wherein the at least one alternative entry portal is adjacent the proximal end of the tongue depressor.

12. A method of using an insertion aid device, the method comprising:
   (a) providing the insertion aid device that comprises (i) a handle; (ii) a tongue depressor pivotally coupled to the handle and comprising a proximal end and a distal end, wherein the tongue depressor is configured to be positioned between 0 degrees and 45 degrees relative to the handle during use; (iii) a first passageway coupled to the tongue depressor; and (iv) at least one additional passageway coupled to the tongue depressor;
   (b) inserting the insertion aid device into a patient's mouth until the distal end of the tongue depressor is placed in contact with a lower portion of the patient's mouth and tongue without entering the patient's throat;
   (c) rotating the tongue depressor relative to the handle until the tongue depressor is oriented 45 degrees relative to the handle; and
   (d) securing the tongue depressor to the handle at the rotated position.

13. The method of claim 12, further comprising the step of performing oral suctioning of the patient via the first passageway.

14. The method of claim 13, wherein the oral suctioning step comprises the steps of:
   (i) coupling a thumb port comprising a hole to an entry portal of the first passageway;
   (ii) connecting a suctioning device to the thumb port;
   (iii) covering the hole of the thumb port; and
   (iv) activating the suctioning device.

15. The method of claim 13, further comprising the step of performing tracheal suctioning of the patient via the at least one additional passageway.

16. The method of claim 15, wherein the tracheal suctioning step comprises the steps of:
   (i) inserting a tracheal suction catheter into the at least one additional passageway until the tracheal suction catheter reaches a desired depth of the patient's trachea; and
   (ii) activating the tracheal suction catheter.

17. The method of claim 12, further comprising the step of deploying a sinus scope, biopsy tool, fiberoptic scope, camera, or breathing tube into the patient via either the first passageway or the at least one additional passageway.

18. An insertion aid device comprising:
   (a) a handle comprising a distal end;
   (b) a tongue depressor comprising:
      (i) a proximal end pivotally coupled to the distal end of the handle, wherein the tongue depressor is configured to be positioned between 0 degrees and 45 degrees relative to the handle during use; and
      (ii) a distal end, wherein the tongue depressor has a progressively smaller cross-sectional shape from the proximal end to the distal end;
   (c) a first passageway comprising:
      (i) an entry portal; and
      (ii) an exit portal adjacent the distal end of the tongue depressor; and
   (d) a guide adjacent the distal end of the tongue depressor, wherein the guide comprises a recess formed by a pair of prongs that extend from the distal end of the tongue depressor, wherein the exit portal is adjacent the recess.

19. The insertion aid device of claim 18, wherein the tongue depressor is configured to be secured to the handle at the 0 degree and the 45 degree positions.

20. A method of using an insertion aid device, the method comprising:
   (a) providing the insertion aid device that comprises (i) a handle, (ii) a tongue depressor pivotally coupled to the handle and comprising a proximal end and a distal end, wherein the tongue depressor is configured to be positioned between 0 degrees and 45 degrees relative to the handle during use, and (iii) a first passageway coupled to the tongue depressor;
   (b) rotating the tongue depressor relative to the handle until the tongue depressor is oriented 45 degrees relative to the handle;
   (c) securing the tongue depressor to the handle at the rotated position; and
   (d) inserting the tongue depressor into a patient's mouth until the distal end of the tongue depressor is placed in contact with a lower portion of the patient's mouth and tongue without entering the patient's throat.

* * * * *